US008217339B2

(12) United States Patent
Kashima et al.

(10) Patent No.: US 8,217,339 B2
(45) Date of Patent: Jul. 10, 2012

(54) ADHERING MATTER INSPECTION EQUIPMENT AND METHOD FOR INSPECTING ADHERING METHOD

(75) Inventors: Hideo Kashima, Kokubunji (JP); Yasuaki Takada, Kiyose (JP); Izumi Waki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 536 days.

(21) Appl. No.: 11/908,516

(22) PCT Filed: Mar. 14, 2005

(86) PCT No.: PCT/JP2005/004461
§ 371 (c)(1),
(2), (4) Date: Dec. 3, 2008

(87) PCT Pub. No.: WO2006/097990
PCT Pub. Date: Sep. 21, 2006

(65) Prior Publication Data
US 2009/0200458 A1    Aug. 13, 2009

(51) Int. Cl.
*H01J 49/26* (2006.01)
*G01N 30/72* (2006.01)

(52) U.S. Cl. ....... 250/288; 250/281; 250/282; 73/23.41; 73/31.01; 73/863.23

(58) Field of Classification Search ............... 73/31.01, 73/31.07, 863.02, 863.03, 863.12, 863.23, 73/23.41, 23.42, 23.3, 23.36, 863, 863.11, 73/863.71, 864.33; 250/281, 282, 288
See application file for complete search history.

(56) References Cited

U.S. PATENT DOCUMENTS

| | | | |
|---|---|---|---|
| 4,987,767 A | 1/1991 | Corrigan et al. | |
| 6,295,860 B1 | 10/2001 | Sakairi et al. | |
| 2002/0078767 A1 | 6/2002 | Jenkins et al. | |
| 2002/0171050 A1* | 11/2002 | Koyama | 250/492.21 |
| 2005/0247868 A1* | 11/2005 | Call et al. | 250/282 |
| 2007/0062256 A1* | 3/2007 | Fine et al. | 73/23.41 |
| 2007/0158447 A1* | 7/2007 | Bunker | 239/1 |

FOREIGN PATENT DOCUMENTS

| | | |
|---|---|---|
| GB | 1 489 928 | 10/1977 |
| JP | 61-59131 | 3/1986 |
| JP | 63-161335 | 7/1988 |
| JP | 02-198333 | 8/1990 |
| JP | 03-51739 | 3/1991 |

(Continued)

*Primary Examiner* — David A Vanore
*Assistant Examiner* — Nicole Ippolito
(74) *Attorney, Agent, or Firm* — Antonelli, Terry, Stout & Kraus, LLP.

(57) ABSTRACT

A technology for collecting a granular substance adhering to a baggage with high rate without touching the substance and inspecting whether a dangerous or specific sample material is adhered to the baggage. A method for simplifying or automating such an inspection is also provided. An adhering matter inspection equipment (1) is characterized in that the equipment comprises a collecting section (5) for collecting a sample material peeled off from an inspection object (25) whereupon the sample material is adhered by blowing compression gas through a capturing filter (52), and an inspecting section (2) for analyzing the sample material captured by the capturing filter (52), and further characterized in that the inspection equipment comprises a section (3) for delivering a baggage to the inspecting section (2), and a carrying section (4) for carrying the capturing filter (52) from the capturing section (5) to the inspecting section (2).

12 Claims, 18 Drawing Sheets

FOREIGN PATENT DOCUMENTS

| | | |
|---|---|---|
| JP | 06-109448 | 4/1994 |
| JP | 07-6729 | 1/1995 |
| JP | 08-033338 | 3/1996 |
| JP | 09-126965 | 5/1997 |
| JP | 9-126966 | 5/1997 |
| JP | 2000-028579 | 1/2000 |
| JP | 2001-041521 | 2/2001 |
| JP | 2001-289769 | 10/2001 |
| JP | 2002-198568 | 7/2002 |
| JP | 2003-120977 | 4/2003 |
| JP | 2003-130766 | 5/2003 |
| JP | 2004-301749 | 10/2004 |

\* cited by examiner

ADHERING MATTER INSPECTION EQUIPMENT AND METHOD FOR INSPECTING ADHERING METHOD

TECHNICAL FIELD

This invention generally relates to a technology for inspecting a substance (sample material) adhered to an inspection object, and particularly to an adhering matter inspection equipment and a method for inspecting an adhering matter, for mainly inspecting a substance adhered to a baggage and a human body.

BACKGROUND ART

Technologies for inspecting a baggage whether or not dangerous materials such as explosives and drugs are hidden in the baggage at a boarding gate of an airport and a port are disclosed, for example, in a patent literature 1, patent literature 2, patent literature 3, and patent literature 4. All technologies disclosed in the patent literatures 1 to 4 are technologies for estimating a substance included in a baggage by inspecting a sample material (granular substance) adhered to a surface of the baggage.

In the patent literature 1, a transfer technology for transferring a sample material which adheres to a baggage surface to a wiping material is disclosed, in which an inspector wipes the baggage surface by the wiping material. In the technology, the transferred sample material is evaporated by heating up the wiping material after the material is wiped. Then, an evaporated gas is ionized, and a mass-to-charge ratio is measured by mass spectrometry to determine whether or not the material is dangerous by comparing the mass-to-charge ratio with those of dangerous materials stored in advance. In addition, instead of the wiping material, a vibrator which contacts a surface of a baggage and vibrates, a heating means which heats up a baggage surface, and a probe which collects an evaporated gas of a sample material or a dangerous material adhering to a baggage surface by, for example, a probe including a blowing means for blowing an air or a suctioning means have been proposed.

In the patent literatures 2 and 3, an adhering matter inspection equipment for inspecting a dangerous material or a gas adhered to a person or an object is disclosed. An automatic baggage inspection technology disclosed in the literatures is a collecting technology of an adhering sample material of a baggage by contacting, for example, springs, sensors, and servos of a sampling head with a baggage surface. The sampling head expands in a whole width of a sampling chamber where the baggage is stored and includes four rotation brushes for wiping an exposed surface of the baggage.

In the patent literature 4, a technology for collecting an air suctioned from a baggage surface in a collection medium which is set at a suctioning outlet is disclosed. Four collection media are placed on a large disc, and one of the four is always placed at the suctioning outlet and another one faces an inlet of an ion mobility spectroscopic analyzer. The disc is rotated at a predetermined angle to peel off a sample material adhered to the baggage and to determine whether or not the sample material is dangerous.

[patent literature 1]: Japanese Laid-open Patent Publication No. 2004-301749.
[patent literature 2]: Japanese Laid-open Patent Publication No. H09-126965.
[patent literature 3]: Japanese Laid-open Patent Publication No. H09-126966.
[patent literature 4]: Japanese Laid-open Patent Publication No. H07-6729.

It is noted that in the technology of the patent literature 1, an inspector has to carefully wipe a whole inspection object with a wiping material. However, there are issues that an inspection condition may be varied due to a variation of a wiping place and a wiping strength depending on each inspector. In addition, a long time is needed for inspecting one inspection object because a whole baggage surface is wiped. Due to the issues described above, a plurality of inspectors are required, thereby resulting in an expensive inspection. Regarding the probe described in the literature 1, there is no description on a condition of a compressed air required for the collecting and on a practical effect. In addition, since an inspector operates the probe, the inspector is required to have a highly-skilled technique for scanning a probe end along a surface of an inspection object, which may have a complex irregularity.

In the rotation brushes disclosed in the patent literatures 2 and 3, since only an outmost external surface of a baggage, which may have a complex irregularity such as a handle and a zipper, comes in contact with the rotation brushes, an inspection area may be limited. In addition, an accident such as a breakage of the baggage surface and a breakage of a good inside the baggage may happen when the rotation brushes are pushed on the baggage surface.

In the patent literature 4, since an air inlet is disposed in one direction, a baggage surface to be inspected may be limited. In addition, since it is required that an air suctioning member, a collection medium for collecting a sample material, and an ion mobility spectroscopic analyzer are arranged on a rotational trajectory of the collection medium mounted on the disc, layouts of the air suctioning member, the collection medium, and the ion mobility spectroscopic analyzer may be limited.

Further, a common issue of the adhering matter inspection technologies described in the patent literatures 1, 2, 3, and 4 is a self-cleaning after a dangerous substance is detected from a baggage. However, there is no practical description for solving the issue.

The present invention has been developed for solving the above issues. It is, therefore, an object of the present invention to provide an adhering matter inspection equipment, which appropriately collects a sample material adhered to a baggage surface without any skilled technique of an inspector, identifies the sample material, and inspects whether or not the sample material includes a dangerous substance (dangerous material). Further, the adhering matter inspection equipment has a self-cleaning function.

DISCLOSURE OF INVENTION

According to a first aspect of the present invention which solves the above issues, there is provided an adhering matter inspection equipment, which includes a collection unit for collecting a sample material on a collection filter by blowing a compressed gas on an inspection object to which the sample material adheres for peeling off the sample material from the inspection object; an inspection unit for analyzing the sample material collected on the collection filter; and at least one nozzle for blowing the compressed gas on a surface of the inspection object with a blowing speed of not less than 20 m/s.

With the constitution described above, the sample material adhered to the inspection object is peeled off by a wind blast of the compressed gas such as an air, and an amount of the sample material collected on the collection filter can be increased, as well as a variation of an inspection condition can be reduced.

In addition, by adding a self-cleaning function, which blows the compressed gas on an inner wall of the collection unit and/or on an arm holding the nozzle, to the adhering matter inspection equipment, an adhering matter inspection equipment which can discharge a remaining sample material and dusts from the collection unit can be built. Using the self-cleaning function, a high reliable inspection can be achieved for the inspection of the next inspection object because a contamination is reduced.

In addition, since the collection filter is returned after being turned over the front-back of the collection filter when the collection filter is inserted into the inspection unit and taken out therefrom, particles remaining on the collection filter can be removed. Therefore, an adhering matter inspection equipment which can continuously use the collection filter without changing the collection filter at every inspection can be built.

According to the present invention, since an amount of peeled off and collected sample material, which is adhered to the inspection object, can be increased without a skilled technique required for the inspector and without touching the inspection object, an adhering matter inspection equipment and a method which can identify the sample material with ease and high reliability are provided. In addition, an adhering matter inspection equipment and a method in which a self-cleaning can be conduct are provided. Further, since the collection filter can be continuously used and the inspection can be automatically conducted, an adhering matter inspection equipment and a method which can improve the operation rate and can reduce a number of people to be required for the inspection are provided.

BRIEF DESCRIPTION OF DRAWINGS

FIG. 4 (b) is an illustration for explaining a change of a signal of a baggage size calculation unit of the adhering matter inspection equipment according to the first embodiment of the present invention;

FIG. 5 (b) is a partial side view for explaining the nozzle driving unit of the adhering matter inspection equipment according to the first embodiment of the present invention;

FIGS. 8 (b), (d) are side views including partial cross sections for explaining the holding method of the collection filter by the collection filter holding means of the adhering matter inspection equipment according to the first embodiment of the present invention;

FIG. 9 (b) is a partial top view including a partial cross section for explaining the heating unit after inserting the collection filter in the adhering matter inspection equipment according to the first embodiment of the present invention;

FIG. 14 (b) is a side view including a partial cross section of the collection filter transportation means for explaining the collection filter transportation means to which the rotation function to turn over a front-back of the hand unit is added in the adhering matter inspection equipment according to the first embodiment of the present invention;

FIG. 17 (*b*) is a side view including a partial cross section for explaining the collection unit of the adhering matter inspection equipment according to the second embodiment of the present invention;

FIG. 19 (*b*) is a front view including a partial cross section for explaining the collection unit of the adhering matter inspection equipment according to the third embodiment of the present invention;

PREFERRED MODE(S) FOR CARRYING OUT THE INVENTION (First Embodiment)

Hereinafter, an embodiment of the present invention will be explained in detail by referring to figures. In the following explanation of the embodiment, a dangerous material such as explosive fine particles or additives of explosives are exemplified as a sample material to be detected by an adhering matter inspection equipment, and a baggage of an examinee to which the dangerous material adheres is also exemplified as an inspection object. However, other than the explosive fine particles or the additives of explosives, an explosive material, a drug such as stimulant drugs, chemicals harmful to a human body, bacteria harmful to a human body, microorganisms such as virus, and the like which contain a sample material generally supposed to be harmful to a human body can be the inspection objects of the adhering matter inspection equipment according to the present invention, as well as a mail, a human body, and imported or exported goods. However, a sample material to be detected by the adhering matter inspection equipment is not limited, and a sample material containing a specific component material may be the inspection object.

Figure 1:
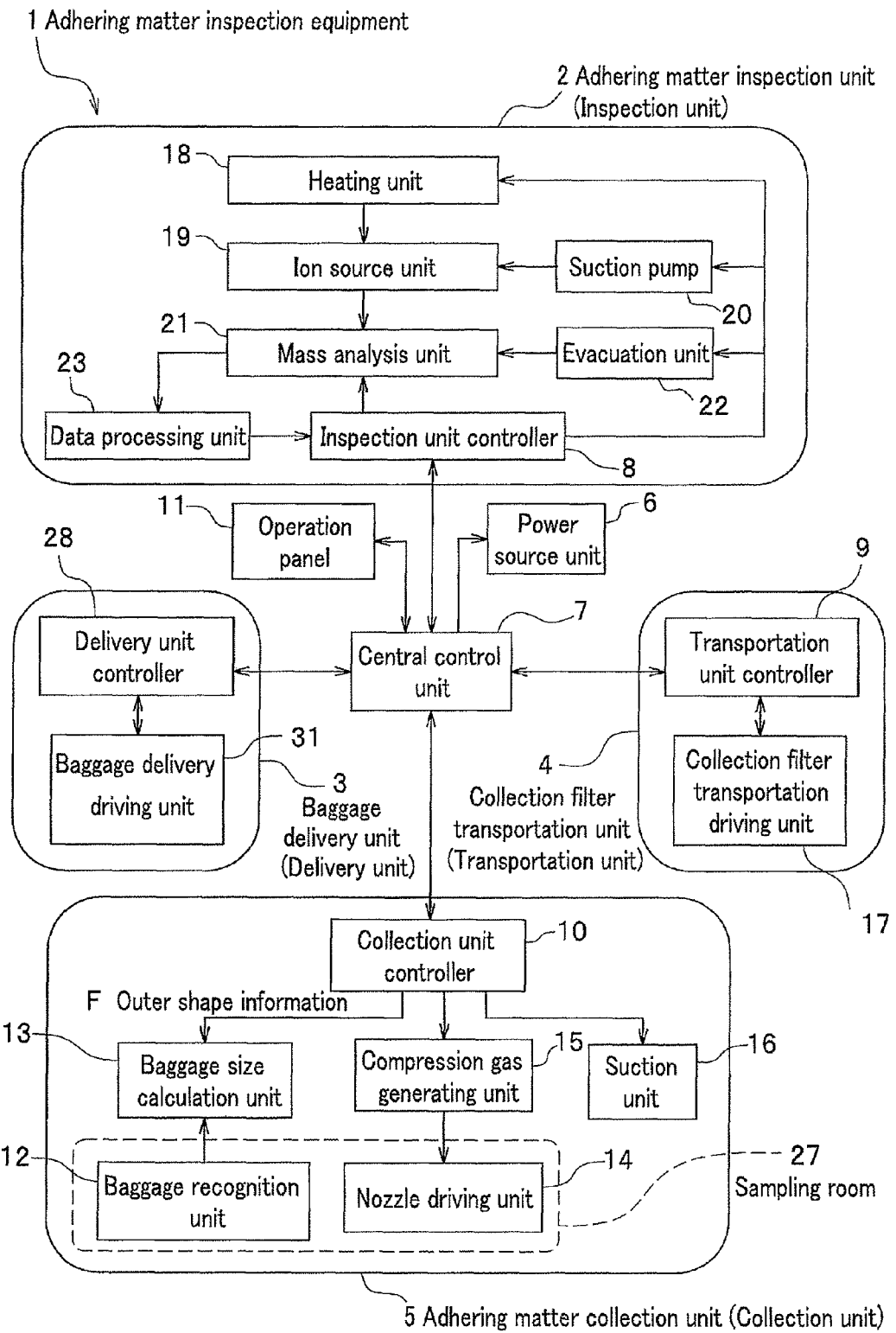
FIG. 1 is a block diagram showing a main constitution of an adhering matter inspection equipment according to a first embodiment of the present invention.

FIG. 1 is a block diagram showing a main constitution of an adhering matter inspection equipment 1 according to a first embodiment of the present invention.

Figure 2:
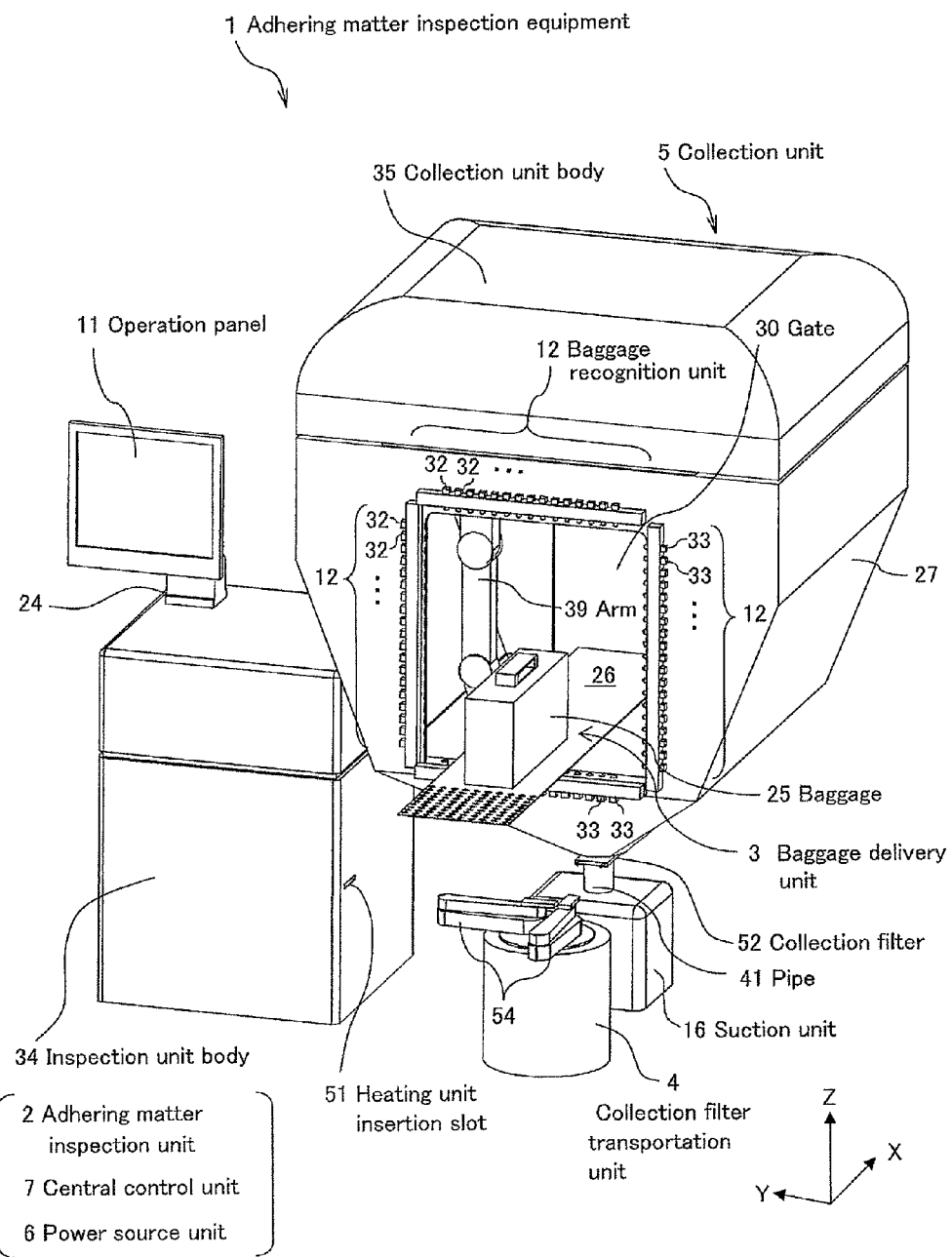
FIG. 2 is a perspective view showing an adhering matter inspection equipment according to the first embodiment of the present invention.

FIG. 2 is a perspective view showing an external view of the adhering matter inspection equipment 1 according to the first embodiment of the present invention.

The adhering matter inspection equipment 1 according to the first embodiment includes an adhering matter inspection unit 2, a baggage delivery unit (delivery unit) 3, a collection filter transportation unit (transportation unit) 4, an adhering matter collection unit (collection unit) 5, a power source unit 6, a central control unit 7, and an operation panel 11. The power source unit 6, which supplies power required for operating each of the units of the equipment, is controlled by the central control unit 7. The central control unit 7 is connected to an inspection unit controller 8, a transportation unit controller 9, a collection unit controller 10, and a delivery unit controller 28. An operation condition of each of the units of the equipment is input from the operation panel 11, and the central control unit 7 controls the operation of the each of the units of the equipment based on the input operation condition.

The central control unit 7 shown in FIG. 1, the power source 6, each component of the adhering matter inspection unit 2, the collection unit controller 10, a baggage size calculation unit 13, and the transportation unit controller 9 are stored inside an inspection unit body 34 shown in FIG. 2. The operation panel 11 is supported by a support member 24 which is movable to a desired position where the operation is easily implemented.

In the adhering matter collection unit 5, a baggage recognition unit (recognition unit) 12, the baggage size calculation unit 13, a nozzle driving unit 14, a sampling room 27, a compression gas generating unit 15, a suction unit 16, and a collection filter 52 (see FIG. 2) are disposed. The baggage recognition unit 12 recognizes an outer shape of an inspection object. The baggage size calculation unit 13 calculates a supposed outer shape of the inspection object based on an output of the baggage recognition unit 12. The nozzle driving unit 14 moves a nozzle 36 (see FIG. 5) along the supposed outer shape of the inspection object, which is calculated by the baggage size calculation unit 13. The sampling room 27 stores the inspection object. The compression gas generating unit 15 generates a compressed gas for blowing an air jet (compressed gas) from the nozzle 36. The suction unit 16 suctions a gas inside the sampling room 27 through a pipe 41 (see FIG. 2) which is connected to a bottom of the sampling broom 27. The collection filter 52 (see FIG. 2) is disposed so as to be capable of inserting and taking out into and from the pipe 41 and collects a sample material which is peeled off from the inspection object by the air jet. Using the adhering matter collection unit 5 constituted as described above, the sample material adhered to a surface of the inspection object is peeled off, and collected on the collection filter 52.

The collection filter 52 (see FIG. 2) on which the sample material is collected is taken out from the pipe 41 by a collection filter transportation driving unit 17 of the collection filter transportation unit 4, and inserted into an oven (heating unit) 18 of the adhering matter inspection unit 2.

The heating unit 18 of the adhering matter inspection unit 2 is maintained at a constant temperature, and heats up the collection filter 52 inserted into the heating unit 18 up to a temperature at which the adhered sample material evaporates. Then, the sample material collected on the collection filter 52 is also heated up, and evaporates to generate a sample gas. The heating unit 18 is connected to an ion source unit 19. The sample gas is introduced into the ion source unit 19 by a suction pump 20, and ionized. Ions generated by the ion source unit 19 are mass-analyzed by a mass analysis unit 21. The ion source unit 19 and the mass analysis unit 21 are evacuated by an evacuation unit 22.

In a storage means of a data processing unit 23, a database which includes standard mass analysis data (value and relative intensity of mass-to-charge ratio (mass of ion/valence of ion)) necessary for identifying the sample material adhered to a baggage 25 is stored. An output signal of a detector of a mass analyzer of the mass analysis unit 21 is transmitted to the data processing unit 23, and a dangerous material (for example, explosives) included in the sample material is identified through data processing of such as cross-checking between the database which is read out from the storage means and a result of the mass analysis of ions originated from the dangerous material.

The identified dangerous material (for example, explosives) and/or the result of the mass analysis are displayed on the operation panel 11.

Figure 3:
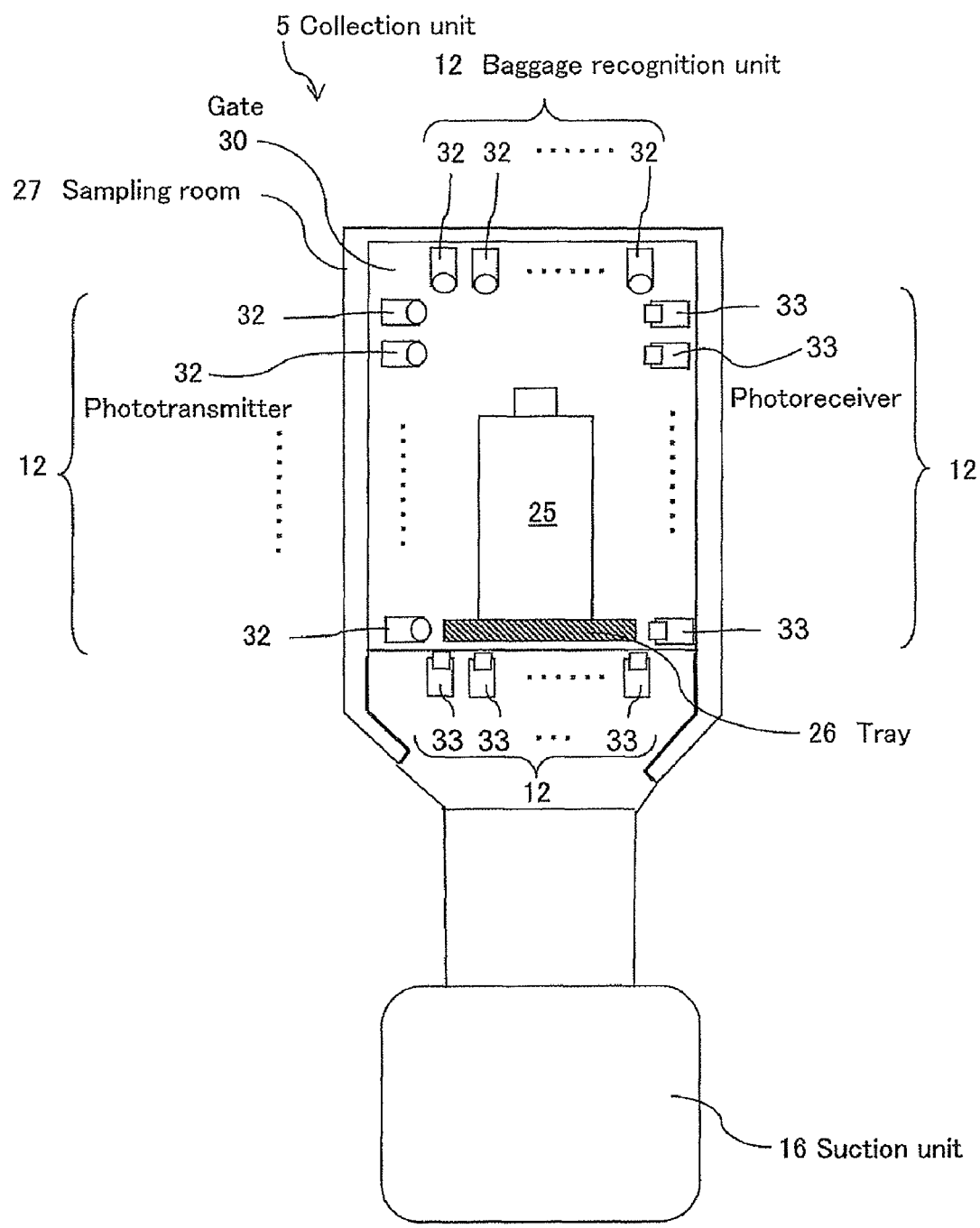
FIG. 3 is a front view for explaining a baggage recognition unit of an adhering matter inspection equipment according to the first embodiment of the present invention.

FIG. 3 is a front view for explaining a constitution of the baggage recognition unit 12 (see FIG. 1) of the adhering matter collection unit 5 of the adhering matter inspection equipment 1 according to the first embodiment of the present invention. The front view of FIG. 3 is a view of the adhering matter inspection equipment 1 as seen from a negative direction of an X-axis in FIG. 2, in which each of the units except the baggage recognition unit 12 is omitted.

The baggage 25, which is an inspection object, is delivered to the sampling room 27 by being placed on a mesh-like metal tray 26 which is driven by the baggage delivery driving unit 31 (see FIG. 1). A speed sensor is installed in the baggage delivery driving unit 31. A signal of the speed sensor is transmitted to the baggage size calculation unit 13 from the delivery unit controller 28 through the central processing unit 7, and the speed is always monitored as a delivery speed of the baggage 25. It is noted that a preferable size of the baggage 25 which is capable of being inspected in the embodiment is about 40 cm wide, 50 cm high, and 70 cm long.

At a gate 30 of the sampling room 27, the baggage recognition unit 12 is disposed outside an opening of 40 cm wide and 50 cm high, which is a maximum size of the baggage 25 capable of being inspected. The baggage recognition unit 12 is equipped with phototransmitters 32, 32, , , , for transmitting lights, which are arranged in line in vertical and horizontal directions, respectively at intervals of 3 cm, and photoreceivers 33, 33, , , , for receiving the lights from the phototransmitters 32, 32, , , , are arranged on opposite sides of the phototransmitters 32, 32, , , , in the vertical and horizontal directions. In the embodiment, the baggage recognition unit 12 is disposed at the gate 30 of the sampling room 27, in which fifteen pairs of the phototransmitter 32 and the photoreceiver 33 and nineteen pairs of the phototransmitter 32 and the photoreceiver 33 are arranged in the horizontal direction and the vertical direction, respectively.

If the baggage 25 blocks a light from a phototransmitter 32, a photoreceiver 33, which faces the phototransmitter 32, of the baggage recognition unit 12 can not receive the light. When an L/H signal (see FIG. 4B) which indicates whether or not the photoreceiver 33 is receiving a light is transmitted to the baggage size calculation unit 13 (see FIG. 1), a cross sectional shape of the baggage 25 is detected. Since the baggage 25 is transported in a longitudinal direction of the tray 26 by the baggage delivery unit 3 (see FIG. 2), an outer shape of the baggage 25 can be obtained by combining the cross sectional shape, which is detected in a short period of time by the baggage recognition unit 12, of the baggage 25.

Figure 4:
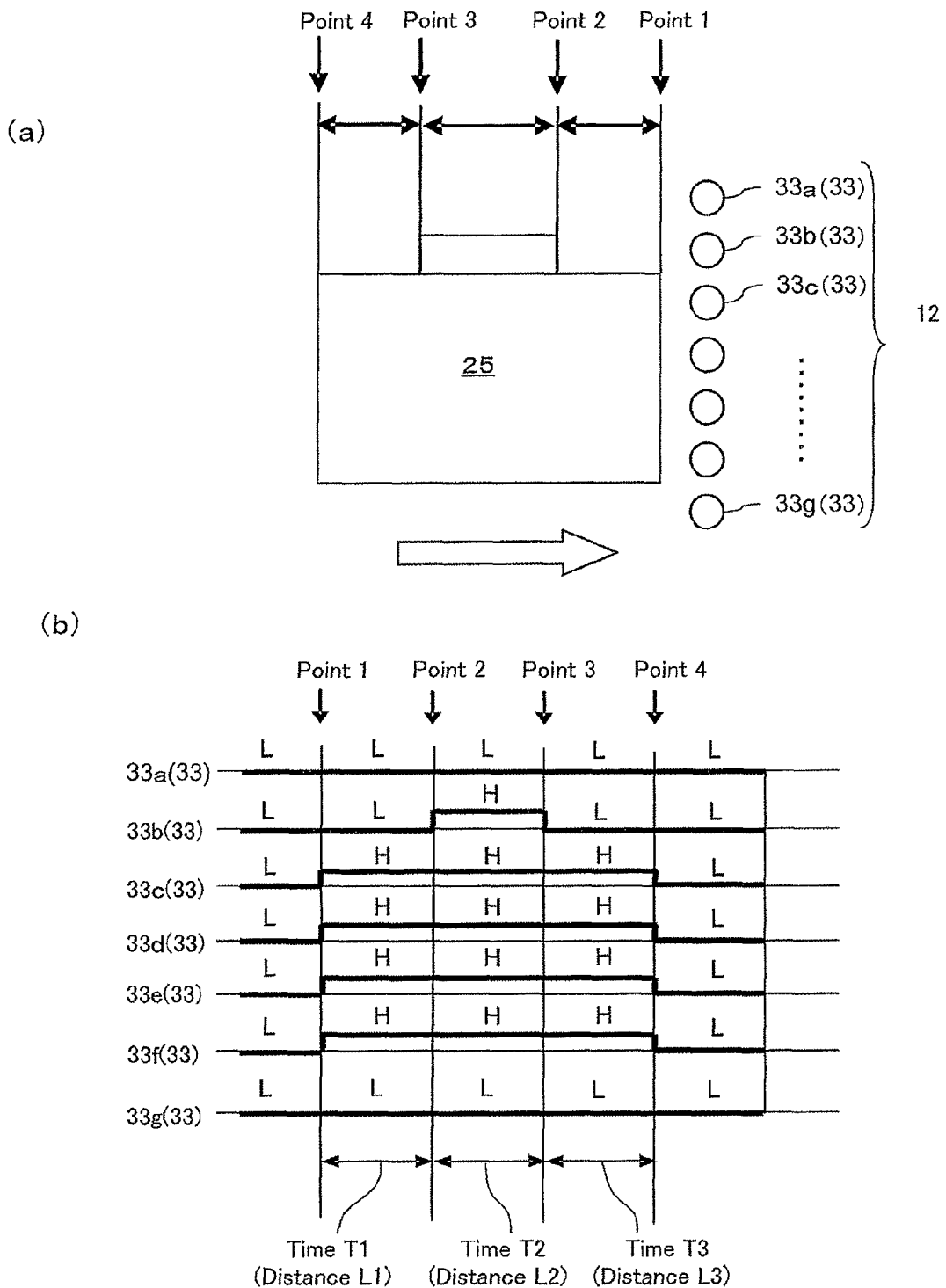
FIG. 4 (a) is a partial side view for explaining a baggage size detection process of an adhering matter inspection equipment according to the first embodiment of the present invention.

FIG. 4 is an illustration for explaining a process for detecting a size of the baggage 25 by the baggage recognition unit 12 which is used in the first embodiment of the present invention.

FIG. 4 (a) is a schematic diagram showing a positional relation between the baggage recognition unit 12 and the baggage 25 as seen from a Y-axis direction in FIG. 2. It is noted that descriptions except for the baggage 25 and the baggage recognition unit 12 are omitted. In FIG. 4 (a), for simplification, the baggage recognition unit 12 is equipped with only seven ptoreceivers 33 (33a, 33b, 33c, , , , 33g) for detecting sizes in height and depth directions of the baggage 25. It is noted that in FIG. 4 (a), means for detecting the sizes in the height and depth directions of the baggage 25 is explained. However, a size in a width direction of the baggage 25 can be detected by a similar baggage recognition unit 12 disposed in upper and bottom directions of the baggage 25.

FIG. 4 (b) is a schematic diagram showing a status of each of the photoreceiver 33 (33a, 33b, 33c, , , , 33g) when cross sections of the baggage 25 corresponding to a point 1, a point 2, a point 3, and a point 4 pass across the baggage recognition unit 12 shown in FIG. 4 (a). In FIG. 4 (b), the horizontal axis indicates a time by seconds. In the figure, an H-signal expresses a status in which the photoreceiver 33 outputs a signal by being blocked a light from the phototransmitter 32, and an L-signal expresses a status in which the photoreceiver 33 outputs no signal by receiving the light from the phototransmitter 32.

The baggage 25 is transported to an arrowed direction in FIG. 4 being placed on the tray 26 (see FIG. 2) of the baggage delivery unit 3 (see FIG. 1). A delivery speed of the baggage 25 is one which is determined based on a signal detected by a speed sensor (not shown) attached to the baggage delivery driving unit 31 (see FIG. 1). In addition, the delivery unit controller 28 controls the baggage delivery driving unit 31 based on a signal from the speed sensor so that the delivery speed of the baggage 25 becomes a predetermined value.

Returning to FIG. 4, the explanation will be continued. When each of the point 1, point 2, point 3, and point 4 of the baggage 25 passes across the baggage recognition unit 12, a signal of the photoreceiver 33 of the baggage recognition unit 12 changes. As shown in FIG. 4 (b), the photoreceiver 33c, the photoreceiver 33d, the photoreceiver 33e, and the photoreceiver 33f detect the baggage 25 at the point 1 which indicates an end face position of the baggage 25. The photoreceiver 33b, the photoreceiver 33c, the photoreceiver 33d, the photoreceiver 33e, and the photoreceiver 33f detect the baggage 25 at the point 2 which indicates a starting point of a protrusion of the baggage 25. The photoreceiver 33b detects no baggage 25 at the point 3 which indicates an ending point of the protrusion of the baggage 25. The all photoreceivers 33 detect no baggage 25 at the point 4 which indicates an ending point of the baggage 25.

Changes of the signals detected by the photoreceivers 33 of the baggage recognition unit 12, as described above, are transmitted to the baggage size calculation unit 13 (see FIG. 1).

In the baggage size calculation unit 13 shown in FIG. 1, a delivery speed of the baggage 25 during a time before each of the signals of the baggage recognition unit 12 is changed is calculated based on a signal output from the speed sensor of the baggage delivery unit 3. Then, a size of an outer shape of the baggage 25 as seen from the side of the baggage 25 is calculated, by using the delivery speed obtained by the result of the calculation, the L-signal/H-signal output from each of the photoreceivers 33 of the baggage recognition unit 12, and a time length before the L-signal/H-signal are changed each other.

The process described above will be explained in detail by referring to FIG. 4 (b).

A distance L1 from the point 1 to the point 2 can be calculated by multiplying T1 by V1, where the T1 is a time length from a detection of the baggage 25 at the point 1 by the photoreceiver 33c, the photoreceiver 33d, the photoreceiver 33e, and the photoreceiver 33f to a detection of the baggage 25 at the point 2 by the photoreceiver 33b, and the V1 is a delivery speed between the point 1 and the point 2. By using a similar calculation, a distance L2 from the point 2 to the point 3 can be calculated by multiplying T2 by V2, where the T2 is a time length from a detection of the baggage 25 at the point 2 by the photoreceiver 33b to no detection of the baggage 25 at the point 3, and the V2 is a delivery speed between the point 2 and the point 3. Also, by using a similar calculation, a distance L3 from the point 3 to the point 4 can be calculated by multiplying T3 by V3, where the T3 is a time length from no detection of the baggage 25 at the point 3 by the photoreceiver 33b to no detection of the baggage 25 by all photoreceivers 33 at the point 4, and the V3 is a delivery speed between the point 3 and the point 4.

A length of the baggage 25 in a depth direction is calculated by adding the L1, L2, and L3, which are obtained by the methods described above.

From the calculations described above, the following outer shape of the baggage 25 can be obtained. The baggage 25 has a size larger than a height of the photoreceiver 33c in the length L1 between the point 1 and the point 2, larger than a height of the photoreceiver 33b in the length L2 between the point 2 and the point 3, and larger than a height of the photoreceiver 33c in the length L3 between the point 3 and the point 4.

Next, a maximum size of the baggage 25 is assumed. In the embodiment, it is supposed that an end face of the baggage 25 is located between a photoreceiver 33 which detected the baggage 25 and a photoreceiver 33 which detected no baggage 25. For example, at the point 1, an actual height of the baggage 25 is supposed to be located between the height of the photoreceiver 33c which actually detected the baggage 25 and the height of the photoreceiver 33b which detected no baggage 25. Since the interval of the photoreceivers 33 in the embodiment is 3 cm, the height of the baggage 25 at the point 1 is supposed to be located at a height 1.5 cm higher than the height of the photoreceiver 33c.

In the method for assuming the maximum size of the baggage 25 described above, since an existence of the baggage 25 between the phototransmitters 32 and the photoreceivers 33 is monitored by a light beam in the embodiment, there is a possibility that the actual baggage 25 may have a height just below the photoreceiver 33b even though the photoreceiver 33b does not react. In this case, the end face of the baggage 25 is located higher than a height supposed by the method described above. In the embodiment, since an interval of a baggage size detector 31 is 3 cm, a maximum error of a size of the supposed baggage 25 is ±1.5 cm. However, there is no problem for peeling off a sample material adhered to a surface of the baggage 25, that is, for achieving the purpose of the present invention. The reason will be described later. In addition, the processing described above is implemented by the baggage size calculation unit 13 during a delivery process of the baggage 25. When a delivery of the baggage 25 in the sampling room 27 is completed, the outer shape calculation of the baggage 25 described above is ended.

Next, a constitution of the nozzle 36 according to the embodiment, from which an air jet for peeling off a sample material is blown, will be explained by referring to FIG. 5.

Figure 5:
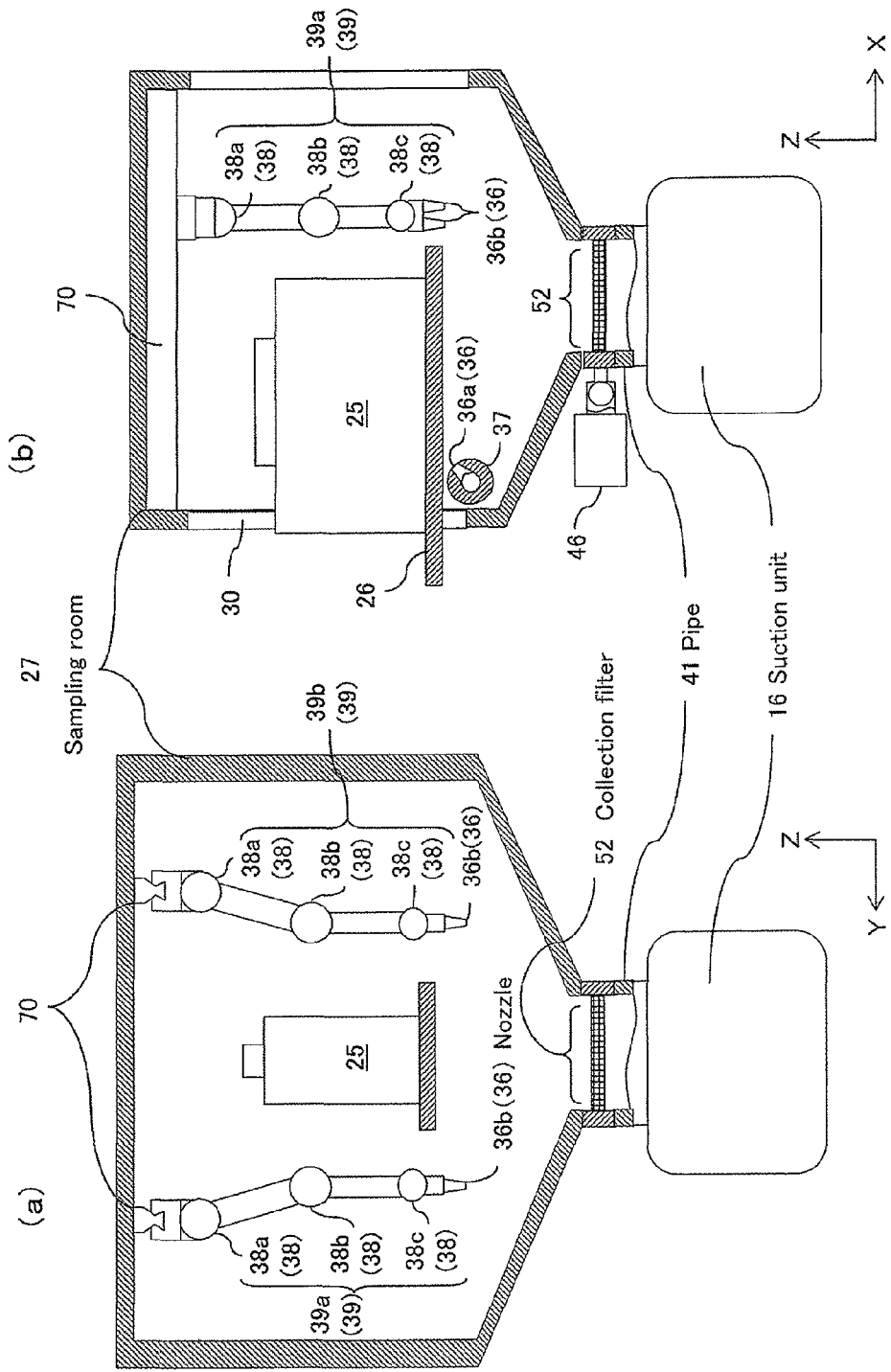
FIG. 5 (a) is a partial front view for explaining a nozzle driving unit of an adhering matter inspection equipment according to the first embodiment of the present invention.

FIG. 5 (a) is a front view including a partial cross section of the sampling room 27. In FIG. 5 (a), the cross section passes through a center of the pipe 41, and it is perpendicular to a baggage transportation direction of the sampling room 27. The front view is a view of the adhering matter inspection equipment in FIG. 2 as seen from the negative direction of the X-axis in FIG. 2, and descriptions of each of the units except for units related to the nozzle 36 will be omitted.

FIG. 5 (b) is a side view including a partial cross section of the sampling room 27. In FIG. 5 (b), the cross section passes through a center of the sampling room 27 and it is perpendicular to the baggage transportation direction of the sampling room 27. The side view is a view of the adhering matter inspection equipment in FIG. 2 as seen from a negative direction of the Y-axis in FIG. 2, and descriptions of each of the units except for units related to the nozzle 36 will be omitted.

The inventors have found the following facts from the experiments. For peeling off a sample material adhered to the baggage 25, it is effective to blow an air jet having a blowing speed of 40 m/s to 130 m/s on a surface of the baggage 25 from an oblique direction against the surface of the baggage 25. In addition, for efficiently collecting the peeled off sample material, it is important to suction a gas inside the sampling room 27, as well as to blow the air jet.

Figure 6:
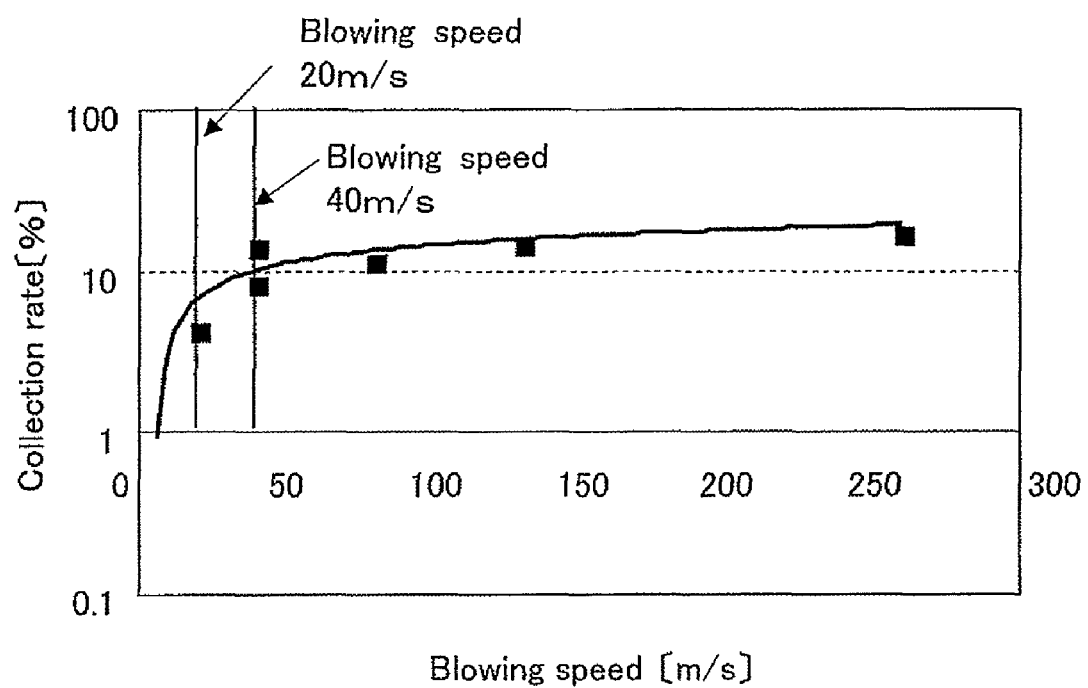
FIG. 6 is a figure for explaining a relation between a collection rate of a C4 explosive and a blowing speed of an air jet in a case of using a configuration of an adhering matter inspection equipment according to the first embodiment of the present invention.

FIG. 6 is a figure showing a result of measurement of a relation between a blowing speed of an air jet and a collection rate of C4 explosive as a sample material to be detected, using a constitution of the adhered matter inspection equipment 1 according to the first embodiment. Here, the C4 explosive is one of plastic explosives. The measurement was implemented as follows. Air jets having different blowing speeds are blown on a surface of leather to which the C4 explosive adheres for collecting the C4 explosive on the collection filter 52. The collection filter 52 is put into the heating unit 18 (see FIG. 7) described later, and a signal intensity of the C4 explosive is measured by the mass analysis unit 21 (see FIG. 9). A collected amount of the C4 explosive has been obtained from the signal intensity of the C4 explosive. It is noted that in the experiment, a diameter of the nozzle 36 is 2 mm so as to widely blow the air jet, and a suctioning rate of a gas inside the sampling room 27 is 1600 liter/minute when the measurement is conducted.

From the result of the experiment in FIG. 6, it was found that a clear signal originated from the C4 explosive can be obtained from the collection filter 5 by blowing the air jet having a blowing speed of not less than 20 m/s. From the experimental result in FIG. 6, it was found that the collection rate of the C4 explosive rapidly increases according to the blowing speed until the blowing speed reaches 40 m/s, and an increment of the collection rate becomes gentle when the blowing speed is not less than 40 m/s. It was also found that the collection rate of the C4 explosive is not largely improved at the blowing speed of, especially, not less than 130 m/s.

In addition, in the experiment in which the air jet is blown on leather without suctioning a gas inside the sampling room 27, an obtained signal intensity originated from the C4 explosive is largely decreased.

Accordingly, it was found that to blow an air jet having a blowing speed of not less than 40 m/s and not more than 130 m/s on a surface of leather and to suction a gas inside the sampling room 27 are important for effectively peeling off and collecting explosive fine particles from the surface of the baggage 25.

In addition, it was found from the experiment that it is necessary to move a tip of the nozzle 36 to a distance of 3 cm to 9 cm from a surface of the baggage 25 in order to blowing the air jet having a blowing speed of 40 m/s to 130 m/s on the surface of baggage 25 from the nozzle 36 (36a, 36b) having a diameter of 2 mm.

In the adhering matter inspection equipment 1 according to the embodiment, as shown in FIG. 5 (a), FIG. 5 (b), the nozzle 36 is equipped with two nozzle systems. One is a nozzle 36a for blowing the air jet on a bottom surface of a baggage and the other is a nozzle 36b for blowing the air jet on upper and side surfaces of the baggage.

The nozzle 36a is disposed on a cylindrical tube 37 which is longer than 40 cm, which is a width of the baggage 25 capable of being inspected. The cylindrical tube 37 is located at 3 cm lower than a transportation track of the tray 26 at the gate 30 of the sampling room 27. Twenty pieces of the nozzles 36a having a diameter of 2 mm are disposed on the tube 37 inclined at 30 degrees to a bottom surface of the tray 26 toward a transportation direction at intervals of 3 cm. The cylindrical tube 37 is rotatable about a central axis of the cylindrical tube 37. A rotational driving of the cylindrical tube 37 is controlled by the nozzle driving unit 14 (see FIG. 1).

The nozzle 36b is movable by a pair of linear traveling mechanisms 70, which are disposed on both sides of the sampling room 27 with respect to a transportation direction of the baggage 25 and capable of traveling in a depth direction of the sampling room 27. The nozzle 36b is held by end portion of each of the arms 39a, 39b having three joints 38 (38a, 38b, 38c) which are rotatably disposed in a plane of the gate 30 of the sampling room 27. A driving of each of the joints 38 of the arm 39 (39a, 39b) is controlled by the nozzle driving unit 14 (see FIG. 1), and two pieces of nozzles 36b having a diameter of 2 mm are disposed on the end of the arm 39 at intervals of 3 cm (see FIG. 5 (b)). It is noted that a number of nozzle 36 and their relative arrangement can be changed as needed.

A turbofan, which is a well-known technology, is used for the compression gas generating unit 15 (see FIG. 1) for blowing an air jet from the nozzle 36 (36a, 36b). The compression gas generating unit 15 is stored in the collection unit body 35 (see FIG. 2) above the sampling room 27, and supplies an air to the nozzle 36 (36a, 36b) by controlling an air volume to be supplied by an air valve, which is not shown. A control of the air valve is controlled by the collection unit controller 10.

A procedure of air jet blowing on the baggage 25 will be explained by referring to FIG. 3 and FIG. 5.

Referring to FIG. 3, first, when the collection unit controller 10 (see FIG. 1) detects an arrival of the baggage 25 at the gate 30 of the sampling room 27 from a signal of the baggage recognition unit 12 which is arranged at the gate 30 of the sampling room 27, the compression gas generating unit 15 (see FIG. 1) is driven, as well as the suction unit 16 for suctioning a gas inside the sampling room 27 is driven. Next, the air valve (not shown) is opened, and a compressed gas is supplied to the twenty pieces of the nozzles 36a shown in FIG. 5 to blow an air jet on the bottom surface of the baggage 25.

At the same time, the nozzle 36b of the arm 39a is arranged on a transportation direction side of the baggage 25, and the nozzle 36b of the arm 39b is arranged on the opposite side of the transportation direction side and above the baggage 25, by operating the nozzle driving unit 14. Then, the air jet having a blowing speed of 40 m/s to 130 m/s is blown on a surface of the baggage 25 keeping a distance of 3 cm to 9 cm away from a supposed outer shape of the baggage 25 calculated by the baggage size calculation unit 13. In the embodiment, the distance is set at 5 cm.

When the collection unit controller 10 determines that the baggage 25 is transported in the sampling room 27 from a signal change of the baggage recognition unit 12, the air valve is closed and air jet bowing from the nozzle 36 is stopped.

As described above, the supposed outer shape of the baggage 25 calculated by the baggage size calculation unit 13 has an error of ±1.5 cm against an actual size of the baggage 25.

In addition, as described above, it is necessary to scan the nozzle 36 against the surface of the baggage 25 from the distance of 3 cm to 9 cm for blowing the air jet having the blowing speed of 40 m/s to 130 m/s on the surface of the baggage 25 from the nozzle 36 having the diameter of 2 mm.

In the embodiment, as described above, a target of traveling position of the nozzle 36 is 5 cm away from the supposed outer shape. In this case, an actual end position of the nozzle 36 is located at a distance of summation of 5 cm, which is the distance of the target of the traveling position of the nozzle 36 from the supposed outer shape, and ±1.5 cm, which is a positional error of the supposed outer shape, and the distance of the summation is an actual distance from the surface of the baggage 25 to the end of the nozzle 36. In the embodiment, the scanning around the baggage 25 is implemented at a distance of 3.5 cm to 6.5 cm apart from an actual outer shape of the baggage 25.

Therefore, in the embodiment, the nozzle 36 is scanned along a surface of the baggage 25 in a range of a distance in which an air jet having the blowing speed of 40 m/s to 130 m/s can be blown, which is effective blowing speed for peeling off explosive fine particles from the baggage 25.

That is, if a constitution illustrated in the adhering matter collection unit 5 of the adhering matter inspection equipment 1 according to the embodiment shown in FIG. 2 is adopted, it is preferable that an interval of the phototransmitters 32, 32, , , , (photoreceivers 33, 33, , , , ), which are arranged in line, of the baggage recognition unit 12 is shorter than a distance in which an air jet having a blowing speed of 40 m/s to 130 m/s can be blown on a surface of the baggage 25. If the interval of the phototransmitters 32, 32, , , , (photoreceivers 33, 33, , , , ) is shorter or wider than the distance in which the air jet having the blowing speed of 40 m/s to 130 m/s can be blown on the surface of the baggage 25, an accident that the tip of the nozzle 36 collides with the surface of the baggage 25 may happen, or the air jet having a blowing speed of 40 m/s can not be blown on the surface of the baggage 25.

Then, the nozzle 36 is lowered to a bottom surface of the baggage 25 while scanning a surface of the baggage 25 longer than the calculated depth of the baggage 25 by the baggage size calculation unit 13 and at a distance of about 5 cm from the supposed outer shape of the baggage 25, by driving each of the joints 38 (38a, 38b, 38c) of the arm 39 and the linear traveling mechanism 70 by the nozzle driving unit 14. When the nozzle 36b reaches a bottom surface of the baggage 25, the collection unit controller 10 closes the air valve, completes the air jet blowing, moves the nozzle 36b in a shelter position, and stops the suction unit 16. Here, a degree of freedom of the arm 39, which is equipped with the nozzle 36, is not limited to the embodiment. If a movable range of the nozzle 36b is expanded by changing the degree of freedom of the arm 9 as needed, scanning of the nozzle 36b along a surface of the baggage 25 can be implemented more accurately. Therefore, the expansion of the movable range of the nozzle 36b is effective for peeling off a sample material adhered to the baggage 25.

At the same time, a completion of the air jet blowing from the nozzle 36b is transmitted from the collection unit controller 10 to the central control unit 7, and further to the transportation unit controller 9. Then, the transportation unit controller 9 instructs to take out the collection filter 52 kept in the pipe 41 of the sampling room 27.

Figure 7:
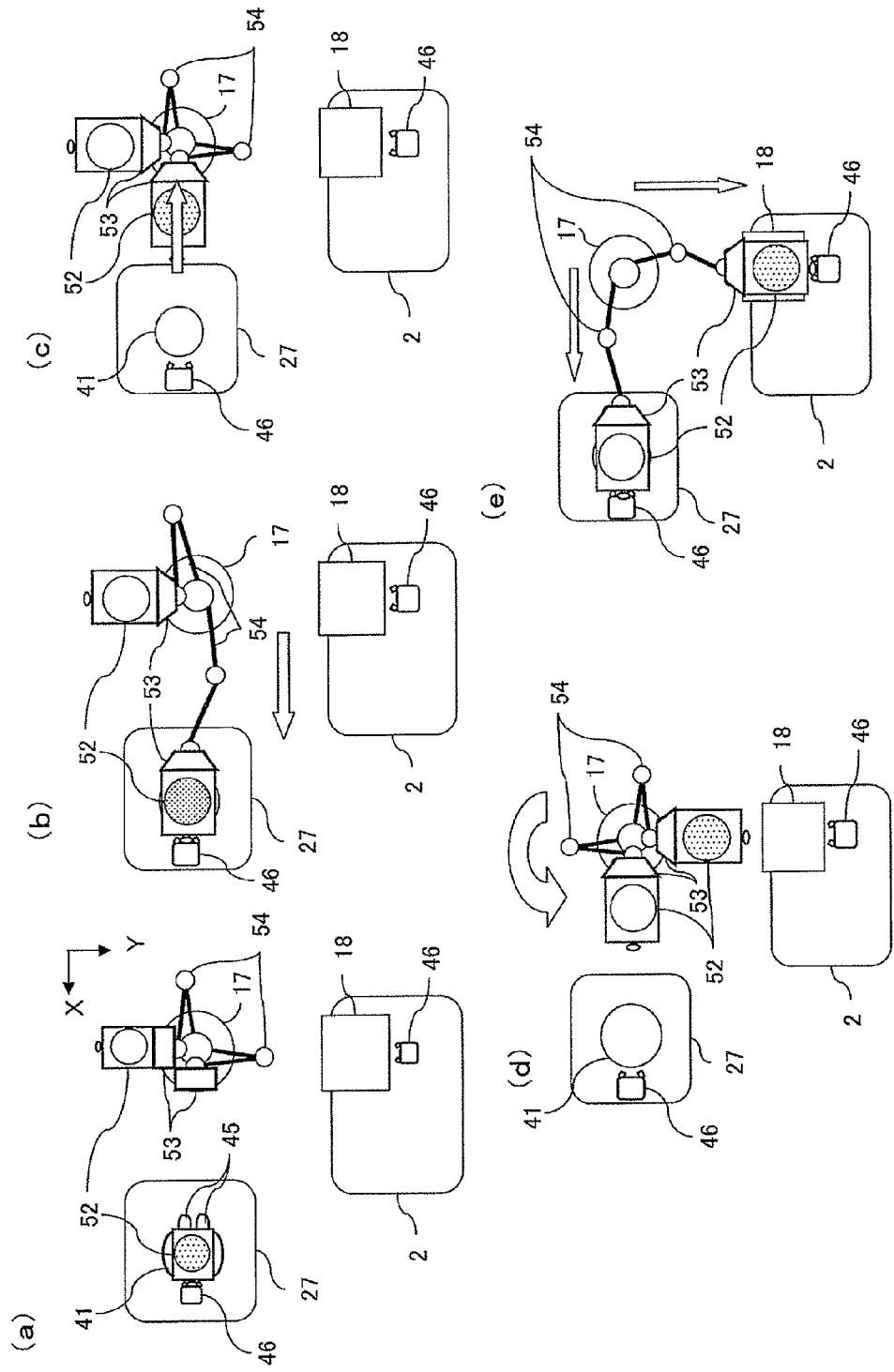
FIGS. 7 (a) to (e) are top views for explaining transportation processes of a collection filter by a collection filter transportation driving unit of an adhering matter inspection equipment according to the first embodiment of the present invention.

FIG. 7 are top views showing a positional relation among the sampling room 27, the adhering matter inspection unit 2, and the collection filter transportation driving unit 17 in the adhering matter inspection equipment 1 according to the embodiment. These top views are top views of the adhering matter inspection equipment 1 as seen from the positive direction of a Z-axis in FIG. 2, and are also schematic diagrams showing each of the units briefly.

Figure 8:
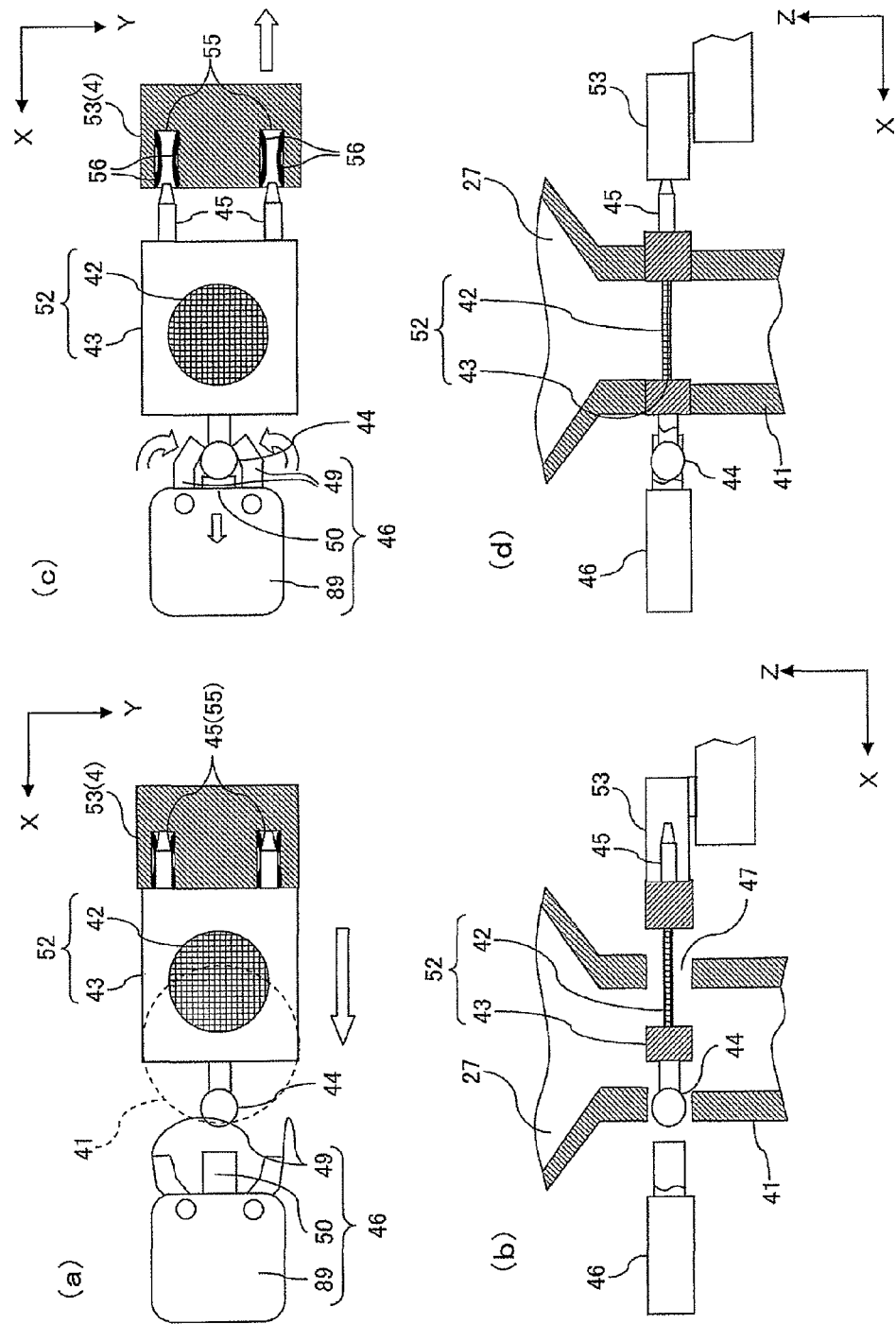
FIGS. 8 (a), (c) are top views including partial cross sections for explaining a holding method of a collection filter by a collection filter holding means of an adhering matter inspection equipment according to the first embodiment of the present invention.

FIG. 8 are illustrations for explaining the collection filter 52 inserted in the pipe 41 which connects the sampling room 27 and the suction unit 16 (see FIG. 2). In addition, FIG. 8 (a) and FIG. 8 (c) are cross sectional views of a part of the pipe 41 keeping the collection filter 52. In FIG. 8 (a) and FIG. 8 (c), the cross sections are partial cross sectional views of the pipe 41 passing through an upper end face of a collection filter inserting port 47 of the pipe 41 as seen from the positive direction of the Z-axis. Each of the units except for the part of the pipe 41, a collection filter holding unit 46, the collection filter 52, a hand unit 53 of the collection filter transportation driving unit 17 is omitted.

FIG. 8 (b) and FIG. 8 (d) are side views of FIG. 8 (a) and FIG. 8 (c) including partial cross sections of FIG. 8 (a) and FIG. 8 (c). In FIG. 8 (b) and FIG. 8 (d), the cross sections are side views passing through a center of the pipe 41 as seen from the positive direction of the Y-axis.

As shown in FIG. 8, the collection filter 52 according to the embodiment is composed of a filter unit 42 and a block frame 43 for supporting the filter unit 42. The filter unit 42 has a circular shape having a diameter of 57 mm which is identical to an inner diameter of the pipe 41. A perimeter of the filter unit 42 is supported by the block frame 43 made of aluminum which has a thickness of 8 mm. One side of the block frame 43 made of aluminum is connected to a sphere 44 having a diameter of 6 mm which is required for fixing the collection filter 52 to the sampling room 27 and the heating unit 18. The other side of the block frame 43 is connected to a cylindrical boss 45 having a diameter of 4 mm which is required for supporting the collection filter 52 by the hand unit 53 when the collection filter 52 is transported by the collection filter transportation driving unit 17.

The inventors found that a minimum size of an explosive particle is 10 micron to 20 micron when the inventors observed a particle size of actual explosives. Based on this knowledge, in the embodiment, a non-penetrating stainless steel filter which is excellent in thermal resistance and endurance, and has a mesh size of 12.7 micron is used. Since the filter has non-penetrability, particles having a diameter from 10 micron to 20 micron can be collected.

The collection filter holding unit 46 for fixing the collection filter 52 to the pipe 41 and the heating unit 18 will be explained by referring to FIG. 8 (a) to FIG. 8 (d).

As shown in FIG. 8 (a) and FIG. 8 (c), the collection filter holding unit 46 fixes the collection filter 52 by catching the sphere 44 which is connected to the block frame 43 of the collection filter 52. The collection filter holding unit 46 is disposed on an opposite side of the collection filter inserting port 47 with respect to the pipe 41 and the heating unit 18 described later, and includes clamps 49 for catching the sphere 44 which is arranged at the end face of the block frame 43, a movable boss 50, and a cam mechanism (not shown) for opening and closing the clamps 49 at a position of the movable boss 50. The cam mechanism is stored in a collection filter holding body 89.

As shown in FIG. 8 (a), if the movable boss 50 of the collection filter holding unit 46 is pushed by the sphere 44 which is connected to the block frame 43 of the collection filter 52, the clamps 49 are closed by a function of the cam mechanism and catch the sphere 44, as shown in FIG. 8 (c). Under this condition, if the collection filter 52 is pulled out after further pushing the sphere 44, as shown in FIG. 8 (a), the clamps 49 are opened by a function of the cam mechanism to release the sphere 44. Pushing and pulling out operations of the collection filter 52 are conducted by the collection filter transportation unit 4.

As shown in FIG. 7, the collection filter transportation driving unit 17 includes a pair of hand units 53 for catching the collection filter 52 and a pair of transportation arms 54 for transporting the collection filter 52 as well as giving a stretching-retracting and rotation freedom to the hand unit 53. Each of the hand units 53 is capable of rotational movement in a desired direction and linear traveling to a desired position. In addition, each of the transportation arms 54 is capable of linear traveling independently. On ends of the hand units 53, as shown in FIG. 8 (c), holes 55 are disposed, in which two bosses 45 which are disposed in the block frame 43 of the collection filter 52 can be inserted. A plate spring 56 which is rolled into a cylindrical shape is set in the holes 55. If the boss 45 of the block frame 43 is inserted in the holes 55, the boss 45 is held by a reaction force of the plate spring 56. Accordingly, the collection filter 52 is held in the hand unit 53.

A procedure for taking out the collection filter 52 from the pipe 41 and inserting it into the heating unit 18 will be explained using FIG. 7 and FIG. 8.

As described above, the collection filter 52 is held in the pipe 41 by the collection filter holding unit 46. As shown in FIG. 7 (b), by stretching the transportation arm 54 of the collection filter transportation driving unit 17, and by inserting the boss 45 of the block frame 43 into the holes 55 of the hand unit 53 as shown in FIG. 8 (c), the collection filter 52 is held. In addition, as shown in FIG. 7 (b) and FIG. 7 (c), if the transportation arm 54 is retracted after stretching the transportation arm 54, as shown in FIG. 8 (a), the clamps 49 of the collection filter holding unit 46 are opened in conjunction with a retracting movement of the transportation arm 54 by a cam mechanism 51, and the collection filter 52 is taken out from the pipe 41. As shown in FIG. 7 (c), after retracting the transportation arm 54 to a predetermined position, the hand unit 53 is rotated to a position facing the heating unit 18 as shown in FIG. 7 (d). As shown in FIG. 7 (e), the transportation arm 54 is advanced again, and the collection filter 52 is inserted into the heating unit 18 from a heating unit inserting port 51 (see FIG. 2). It is noted that the filter holding unit 46 is also disposed on an opposite side of the collection filter transportation unit 4 of the heating unit 18, and the collection filter 52 inserted into the heating unit 18 is held by this filter holding unit 46.

In the embodiment shown in FIG. 7 (e), an example is shown, in which the collection filter transportation driving unit 17 inserts the collection filter 52 into the heating unit 18, while inserting another collection filter 52 into the pipe 41 of the sampling room 27 by stretching the transportation arm 54 which holds the another collection filter 52 on the hand unit 53 to prepare for the inspection of the next baggage 25.

Figure 9:
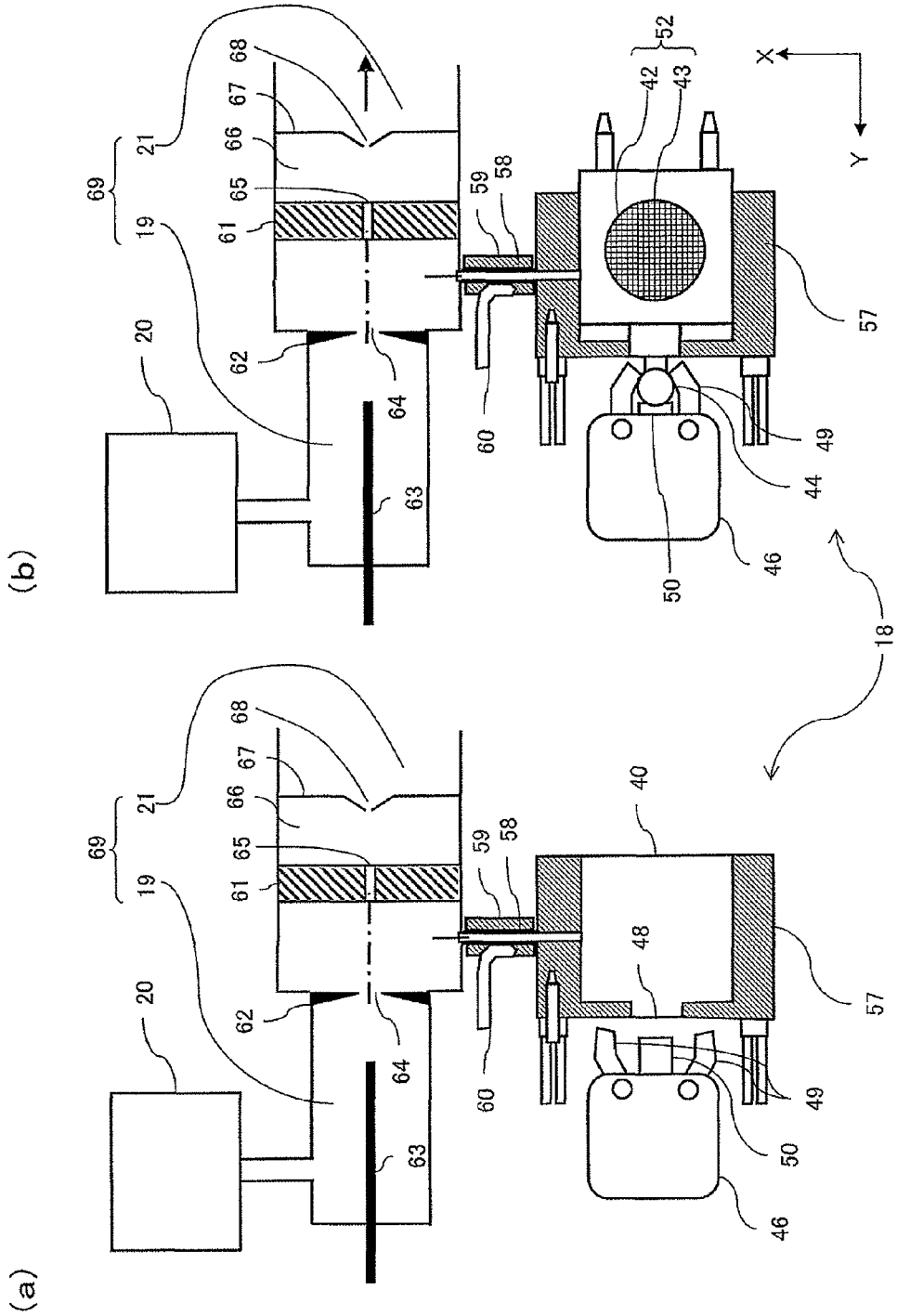
FIG. 9 (a) is a partial top view including a partial cross section for explaining a heating unit before inserting a collection filter in the adhering matter inspection equipment according to the first embodiment of the present invention.

Next, a brief constitution of the heating unit 18 of the adhering matter inspection unit 2 will be explained using FIG. 9. FIG. 9 is a top view showing partial cross sectional views of the heating unit 18, the ion source unit 19, and the mass analysis unit 21. In FIG. 9, the cross section passes through a center axis of an introduction pipe 58, and the top view is a view as seen from the positive direction of the Z-axis. The heating unit 18, the ion source unit 19, the mass analysis unit 21, and the suction pump unit 20 are simplified in FIG. 9, and other constitutional units except for the units described above are omitted.

As shown in FIG. 9, a basic constitution of the heating unit 18 is composed of a boxy storage unit 57, the collection filter holding unit 46 for holding the collection filter 52, the introduction pipe 58 for connecting the ion source unit 19 and the heating unit 18, a heat source 59 which is disposed in the storage unit 57 and the introduction pipe 58 for preventing a sample gas from being absorbed or promoting desorption of the sample gas, and a thermometer 60 for measuring a temperature. The thermometer 60 and the heat source 59 are connected to the inspection unit controller 8 (see FIG. 1), and the temperature can be controlled at a desired temperature. The storage unit 57 and the introduction pipe 58 can be heated and controlled at a desired temperature between a room temperature and 300° C. In the embodiment, temperatures of the storage unit 57 and the introduction pipe 58 are set at 200° C.

In the storage unit 57 of the heating unit 18, a heating unit insertion slot 51 from which the collection filter 52 is inserted and a window 48 are disposed. The window 48 is disposed on an opposite side of the heating unit insertion slot 51 and through which the sphere 44, which is disposed on the block frame 43 of the collection filter 52, passes.

A procedure for inserting the collection filter 52 from an insertion slot 40 of the heating unit 18 into the heating unit 18 will be explained by referring to FIG. 7 and FIG. 9.

As shown in FIG. 7 (e), the collection filter 52 held by the hand unit 53 is inserted in the storage unit 57 through an insertion slot 47 by stretching the transportation arm 54. Then, as shown in FIG. 9 (b), the sphere 44 disposed in the block frame 43 of the collection filter 52 is pushed to the movable boss 50 of the collection filter holding unit 46 which is disposed outside the storage 57 after passing through the window 48 of the storage unit 57. Further, the sphere 44 disposed in the block frame 43 of the collection filter 52 is held by the clamps 49 of the collection filter holding unit 46 by stretching the transportation arm 54 (see FIG. 7 (e)). Then, the collection filter and the hand unit 53 are separated by retracting the transportation arm 54 and the transportation arm 54 is moved to a shelter position. As a result, as shown in FIG. 9 (b), the collection filter 52 can be kept in the storage unit 57 with a surface thereof up, on which a sample material is collected. Since the insertion slot 40 and the window 48 of the storage unit 57 are closed by the block frame 43 of the collection filter 52, a heating of the collection filter 52 can be implemented efficiently.

If the collection filter transportation driving unit 17 according to the embodiment is used, since only the collection filter 52 is kept in the pipe 41 and the heating unit 18, there is no possibility of mutual contamination between the collection filters 52 through the collection filter transportation driving unit 17. In addition, since only the collection filter 52 is heated up in the heating unit 18, there is no possibility that detection sensitivity of the adhering matter inspection unit 2 is lowered by a gas generated from the hand unit 53 and the transportation arm 54 of the collection filter 52. In addition, in the embodiment, since the sampling room 27 and the heating unit 18 can be arranged at places physically separated one another, the adhering matter collection unit 5 and the adhering matter inspection unit 2 can be arranged freely without increasing a floor space occupied by the units.

As shown in FIG. 9 (b), when the collection filter 52 is inserted into the storage unit 57, since a surface of the collection filter 52 is rapidly heated, vaporization of a sample material collected on the collection filter 52 is rapidly promoted.

A sample gas generated in the heating unit 18 is transferred to a space between a first electrode 61 with a pinhole (hereinafter, referred to as first pinhole electrode 61) and an electrode 62 facing the first pinhole electrode 61 (hereinafter, referred to as facing electrode 62) of the ion source unit 19 through an introduction pipe 58 by the suction pump 20. A pin electrode 63 is arranged in the ion source unit 19, and a high voltage is applied between the pin electrode 63 and the facing electrode 62. Since a corona discharge is generated around an edge of the pin electrode 63, firstly, for example, nitrogen, oxygen, and water vapor are ionized. These ions are called as primary ions. The primary ions move to the facing electrode 62 by an electric field. The vaporized sample gas transferred to the space between the first pinhole electrode 61 and the facing electrode 62 flows into a space where the pin electrode 63 is arranged through an opening 64 disposed in the facing electrode 62, and reacts with the primary ions to be ionized. An ionization method for ionizing a chemical material in a gas by utilizing a chemical reaction between primary ions and the gas, in which the primary ions are generated by utilizing the corona discharge in the atmosphere, is called as an atmospheric pressure chemical ionization method.

A heat source (not shown) and a thermometer (not shown) are installed in the ion source unit 19. A power supply to the heat source is controlled by the inspection unit controller 8 (see FIG. 1) based on an output signal of the thermometer. The ion source unit 19 is always heated and kept at a desired temperature so that the vaporized sample gases do not adsorb inside the ion source unit 19.

A potential difference between the facing electrode 62 and the first pinhole electrode 61 is about 1 kV, and the ions are moved in a direction of the pinhole electrode 61 and incorporated into a differential pumping unit 66 through a first ion introduction pinhole 65. Since adiabatic expansion occurs in the differential pumping unit 66, for example, solvent molecules adhere to the ions, a so-called clustering occurs. It is preferable to heat the first pinhole electrode 61 and a second electrode 67 with a pinhole (hereinafter, referred to as second pinhole electrode 67) by, for example, a heater for reducing the clustering.

Ions of the sample gas generated by the atmospheric pressure chemical ionization method are introduced into the mass analysis unit 21 through the first ion introduction pinhole 65 of the first pinhole electrode 61, the differential pumping unit 66 which is evacuated by an evacuation unit 22 (see FIG. 1), and the second ion introduction pinhole 68 of the second pinhole electrode 67. The mass analysis unit 21 is evacuated by the evacuation unit 22. The ion source unit 19 and the mass analysis unit 21 constitute a single chamber 69.

The ions of the sample gas introduced into the mass analysis unit 21 are mass-analyzed by an ion trap mass spectrometer. In the data processing unit 23 (see FIG. 1), values of mass-to-charge ratios necessary for identifying a single or a plurality of sample materials are set in advance. An output signal of a detector of the mass spectrometer relating to the mass-to-charge ratio necessary for identifying the sample material to be detected is continuously transmitted to the data processing unit 23 with a predetermined time interval as a result of the mass analysis of the sample gas ions. In a storage means of the data processing unit 23, mass analysis data (values of mass-to-charge ratio and relative intensity of the values) necessary for identifying a specific sample material (dangerous material) such as a plurality of explosives and drugs and a determination threshold value of a signal intensity which is a standard for identifying the specific sample material (dangerous material) are stored as a database. A mass-to-charge ratio of a signal transmitted to the data processing unit 23 is compared with the database read out from the storage means. If the sample material is identified to be the specific sample material (dangerous material) of a detection target and if the transmitted signal intensity is larger than that of the determination threshold, existing possibility of the specific sample material (dangerous material) is displayed on the operation panel 11 to notify the possibility to the operator.

Figure 10:
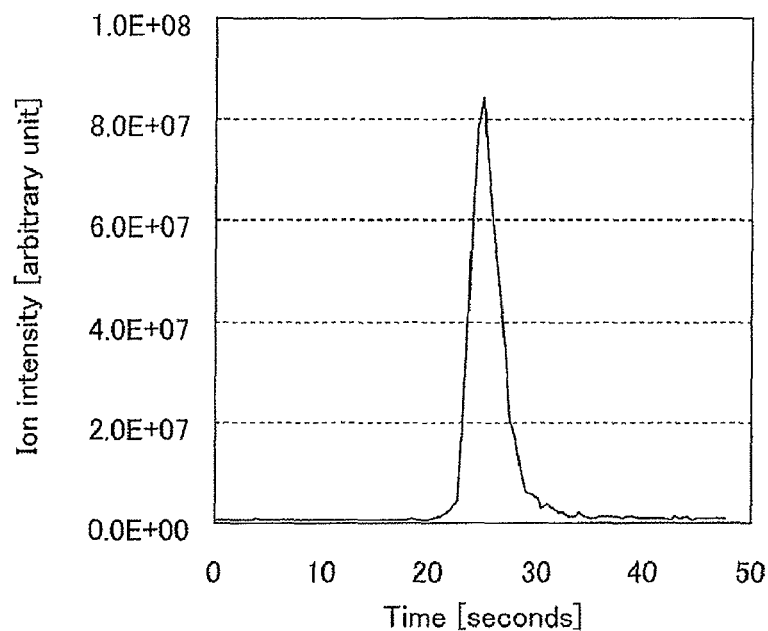
FIG. 10 is a figure showing a time dependence of a signal intensity of a mass-to-charge ratio of a C4 explosive component detected from a baggage to which C4 explosive particles adhere in the adhering matter inspection equipment according to the first embodiment of the present invention.

FIG. 10 is a figure showing a result of an inspection of the baggage 25 to which C4 explosive particles adhere, by using a constitution of the adhering matter inspection equipment 1 according to the first embodiment. In FIG. 10, a vertical axis indicates ion intensity with an arbitrary unit, and a horizontal axis indicates a time by seconds.

As shown in FIG. 10, a clear signal showing a detection of a C4 explosive component can be obtained. From the result, it is proved that the C4 explosive particles are peeled off by an air jet from the actual baggage 25 to which the C4 explosive particles adhere, collected on the collection filter 52, and vaporized by the heating unit 18, and also the C4 explosive component can be detected by the mass analysis unit 21, by using the adhering matter inspection equipment 1 according to the first embodiment. In the adhering matter inspection equipment 1 composed of the constitution according to the embodiment, it is proved from experiments that an average collection rate of the C4 explosive from the baggage 25 is 7.9%.

Figure 11:
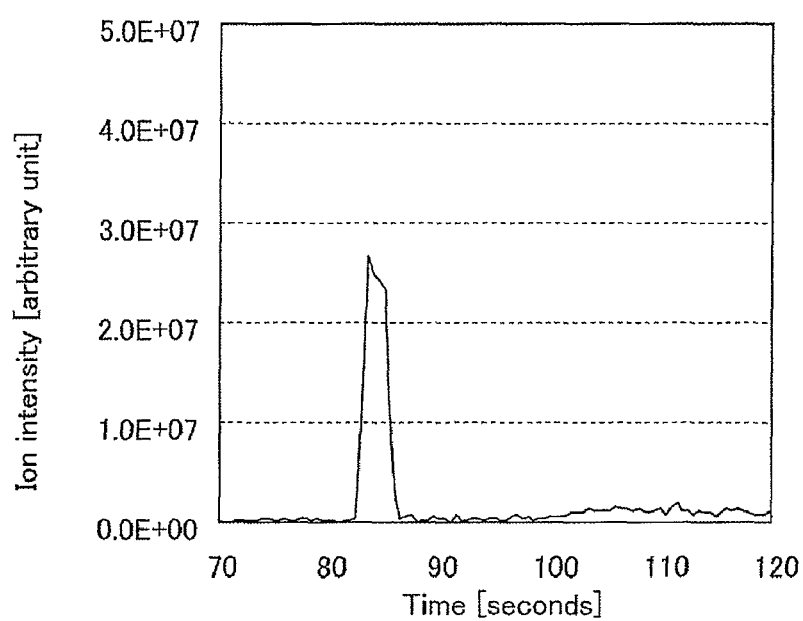
FIG. 11 is a figure showing a time dependence of a signal intensity of a mass-to-charge ratio of a TNT explosive component detected from a baggage to which TNT explosive particles adhere in the adhering matter inspection equipment according to the first embodiment of the present invention.

FIG. 11 is a figure showing a result of an inspection of an actual baggage 25 to which TNT explosive particles adhere.

In FIG. 11, a vertical axis indicates ion intensity with an arbitrary unit, and a horizontal axis indicates a time by seconds. As shown in FIG. 11, a clear signal showing a detection of the TNT explosive component can be obtained. From the result, it is proved that the TNT explosive particles are peeled off by an air jet from the actual baggage 25 to which the TNT explosive particles adhere, collected on the collection filter 52, and vaporized by the heating unit 18, and also the TNT explosive component can be detected by the mass analysis unit 21, using the adhering matter inspection equipment 1 according to the first embodiment.

In the adhering matter inspection equipment 1 according to the embodiment described above, an inspection for determining whether or not dangerous materials such as explosives are included in a sample material adhered to the baggage 25 can be implemented without touching the baggage 25, and can be implemented automatically under a constant condition. Accordingly, the inspection can be rapidly implemented without causing, for example, a breakage and contamination of the baggage 25, as well as no skilled inspector is required for the inspection.

Effects of the adhering matter inspection equipment according to the first embodiment are summarized as follows.
(1) Since in the sampling room 27, an air jet having a blowing speed of 40 m/s to 130 m/s, which is effective for peeling off a sample material adhered to the baggage 25, can be blown on a surface of the baggage 25 by scanning the nozzles 36 around the baggage 25 at a distance 5 cm away from a supposed outer shape of the baggage 25 calculated by the baggage size calculation unit 13, the sample material can be effectively peeled off from the baggage 25.
(2) The peeled off sample material can be effectively collected on the collection filter 52 by suctioning a gas inside the sampling room 27 through a non-penetrating collection filter 52, which is fixed at a bottom of the sampling room 27.
(3) Since the collection filter 52 on which the sample material is collected is automatically taken out from the sampling room 27 by the collection filter transportation driving unit 17 and inserted into the heating unit 18 connected to the mass analysis unit 21, the collection filter 52 can be transported from the sampling room 27 to the heating unit 18 without contamination during the transportation process of the collection filter 52 and by a human being.
(4) Since the collection filter 52 inserted into the heating unit 18 is rapidly heated up, a component of a dangerous material (for example, explosives) included in the sample material vaporizes to generate a dense gas. As a result, an ion intensity of ions generated in the ion source unit 19 and originated from the dangerous material becomes high. Accordingly, a higher signal intensity can be obtained by the mass analysis unit 21, thereby resulting in high sensitive inspection.

Next, a self-cleaning procedure of the adhering matter inspection equipment 1 according to the embodiment will be explained.

Figure 12:
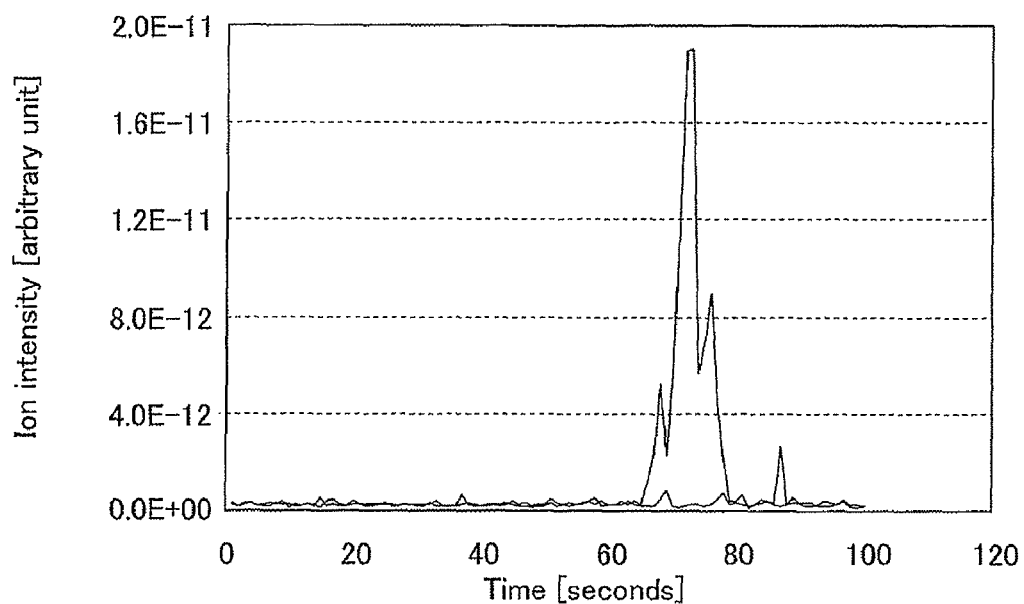
FIG. 12 is a figure showing a time dependence of a signal intensity of a mass-to-charge ratio of a C4 explosive component detected from a collection filter on which a sample material is collected by blowing an air jet on an inner wall of a sampling room where a C4 explosive component has been detected in the adhering matter inspection equipment according to the first embodiment of the present invention.

FIG. 12 is a figure showing a result of an inspection for determining whether there exist explosives or not by inserting a collection filter in the heating unit 18, by using the adhering matter inspection equipment 1 according to the first embodiment. The collection filter is one which is used when an air jet is blown on an inner wall of the sampling room 27 where the C4 explosive is detected, while suctioning a gas inside the sampling room 27 by the suction unit 16. In FIG. 12, a vertical axis indicates ion intensity with an arbitrary unit, and a horizontal axis indicates a time by seconds. As shown in FIG. 12, a signal indicating the C4 explosive (dangerous material) is obtained from a sample material sampled from the sampling room 27 where a clear signal of the C4 explosive is detected.

From the result in FIG. 12, the inventors found that explosive particles (dangerous materials) remain in the sampling room 27 if a dangerous material such as explosives was once sampled in the sampling room 27. It is considered that if the next baggage 25 is inspected under a condition that the dangerous material remains on the inner wall of the sampling room 27, the dangerous material adhered to the inner wall of the sampling room 27 is peeled off and collected on the collection filter 52. In this case, although the dangerous sample material is not actually adhered to the sample material adhered to the baggage 25, the dangerous material is detected by the adhering matter inspection unit 2, thereby resulting in an incorrect detection. Therefore, a self-cleaning function is an essential function for the adhering matter inspection equipment 1 of the baggage 25.

It may be possible that an inspector carefully wipes the inner wall of the sampling room 27 with a clean wiping material for cleaning the inner wall of the sampling room 27. However, the method described above is not practical, considering a safety of the inspector, a time needed for the cleaning, a breakage of, for example, the arm 39 equipped with the nozzle 36 and the baggage recognition unit 12 which are installed in the sampling room 27, and contamination of the inner wall of the sampling room 27 by a human being. Therefore, an automatic self-cleaning function for cleaning the inner wall of the sampling room 27 is required for the adhering matter inspection equipment 1 of the baggage 25.

There exist two issues for the self-cleaning function.
(1) One issue is that a time needed for the self-cleaning must be short so as to start the next inspection as soon as possible.
(2) The other issue is that a cleaning effect must be checked quantitatively so as to avoid an incorrect detection.

In the adhering matter inspection equipment 1 according to the first embodiment, the self-cleaning of the sampling room 27 can be automatically implemented without involving a human being, and without any specific component and unit for the self-cleaning. In addition, effects of the cleaning can be inspected quantitatively in the adhering matter inspection equipment 1.

The self-cleaning of the adhering matter inspection equipment 1 according to the first embodiment is implemented by the following procedure.

If it is determined by the data processing unit 23 based on the inspection result that an explosive component is detected, the detection is notified to the inspector by displaying the detection on the panel 11. After that, the adhering matter inspection equipment 1 becomes a waiting status for starting the self-cleaning. If an inspector selects a self-cleaning operation from the operation panel 11, the central control unit 7 outputs an instruction of the self-cleaning process to the collection unit controller 10, to the transportation unit controller 9, and to the inspection unit controller 8.

In the collection unit controller 10, a normal inspection process is stopped and the self-cleaning process, which is defined in advance, starts. The self-cleaning process is implemented by the following processes. The sampling room 27 is suctioned by driving the suction unit 16, and the compression gas generating unit 15 is also driven. The cylindrical tube 37 is rotated by the nozzle driving unit 14 so that the nozzle 36a arranged in the sampling room 27 is directed to the inner wall of the sampling room 27, and the arm 39 (39a, 39b) is driven by the nozzle driving unit 14 so that the nozzle 36b moves to a self-cleaning starting position which is determined in advance.

After completing the movement of the nozzle 36 (36a, 36b), an air valve (not shown) is opened to supply a compressed gas to the nozzle 36, and an air jet is blown on the inner wall of the sampling room 27. In addition, each of the nozzles 36 (36a, 36b) mutually blows the air jet alternately on each surface of the arm 39 (39a, 39b) on which the nozzle 36 is set.

The inner wall of the sampling room 27 and the mutual surfaces of the arms 39 (39a, 39b) are scanned by the nozzle 36 at a distance of not more than 9 cm, which is a distance between a tip of the nozzle 36 and the inner wall of the sampling room 27 and a distance that an air jet having a blowing speed of not less than 40 m/s, with which explosive fine particles are effectively peeled off, can be blown.

It has been demonstrated that explosive fine particles can be peeled off from the baggage 25 by blowing an air jet. Therefore, the explosive fine particles may be exhausted from the sampling room 27 by blowing the air jet on the inner wall of the sampling room 27, thereby peeling off the explosive fine particles remaining on the inner wall of the sampling room 27 and suctioning a gas inside the sampling room 27 by the suction unit 16. Next, a self-inspection is implemented for checking whether or not the sampling room 27 has a cleanness level identical to that before a detection of a dangerous material.

In the self-cleaning, the collection filter 52 kept in the pipe 41 is taken out by the collection filter transportation driving unit 17 and inserted into the heating unit 18, and a component detected from the collection filter 52 by the adhering matter inspection unit 2 is compared with a component of the dangerous material, which is stored in advance. From a result of the comparison, if it is determined by the adhering matter inspection unit 2 that the cleanness level is a level of no signal detection of explosives, the normal inspection process is restarted, and if determined that the cleanness level is a signal detection level of explosives, the self-cleaning process is started again.

Figure 13:
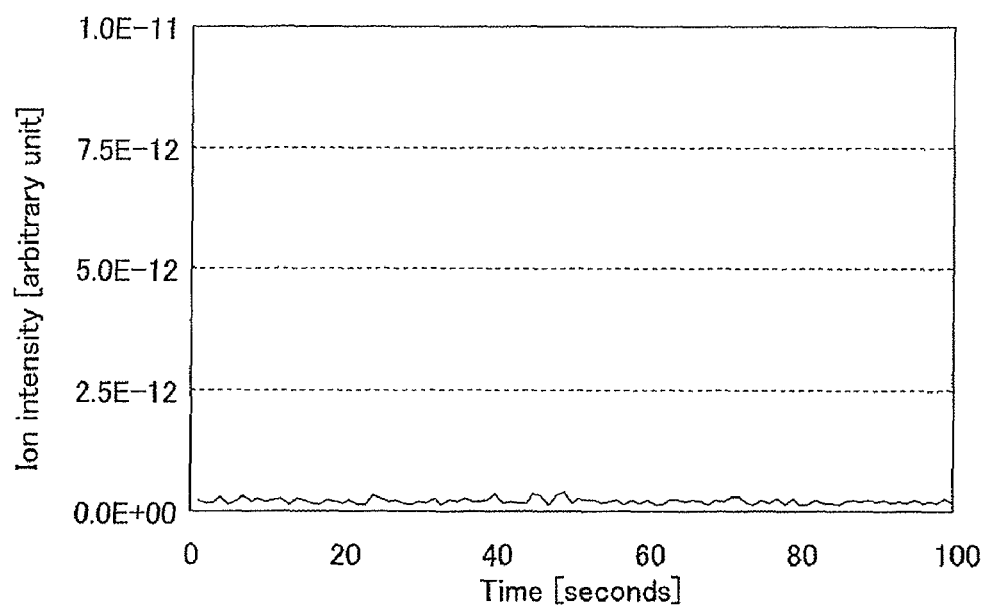
FIG. 13 is a figure showing a time dependence of a signal intensity of a mass-to-charge ratio of a C4 explosive component detected from a collection filter on which a sample material is collected by blowing an air jet on an inner wall of a sampling room after self-cleaning, where a C4 explosive component has been detected in the adhering matter inspection equipment according to the first embodiment of the present invention.

FIG. 13 is a figure showing a result of an inspection of the collection filter 52 which is used during the above-described self-cleaning of the inner wall of the sampling room 27 where the C4 explosive is detected, by using the adhering matter inspection equipment 1 according to the first embodiment. FIG. 13 shows an inspection result after the above-described self-cleaning is repeated eight times. As shown in FIG. 13, since there is no peak on a signal indicating the C4 explosive, it has been proved that the sampling room 27 was cleaned up by the self-cleaning method according to the embodiment.

Using the self-cleaning method according to the embodiment described above, even if explosives are detected once from a baggage, a cleaning inside the sampling room 27 can be automatically implemented in a short time without contamination by a human being and without breakage of components inside the sampling room 27. In addition, since the effect of the cleaning can be checked quantitatively by measuring the cleanness level of the sampling room 27 after the cleaning is implemented by the adhering matter inspection unit 2, there is no possibility of incorrect detection even after detection of a dangerous material. It is noted that a measurement of the self-cleaning effect is not always required to be conducted at every self-cleaning. A time needed for the self-cleaning can be shortened by measuring the self-cleaning effect after a predetermined cycle of the self-cleaning is conducted. In addition, since the collection filter 52, from which a dangerous material is detected, is inserted into the heating unit 18 again and heated up during the blowing of the air jet on the sampling room 27, the dangerous material can be removed even if a component originated from the dangerous material remains. Accordingly, the self-cleaning can be implemented efficiently.

Next, an adhering matter inspection equipment which uses the constitution of the adhering matter inspection equipment 1 according to the present invention will be explained, in which a continuous inspection can be implemented without changing the collection filter 52 at each inspection. It is estimated that a huge number of adhering matter inspections of the baggage 25 may be implemented in a day, even though it depends on the inspection place.

Generally, solid matters such as metal and earth and sand, which are not vaporized by heating, are adhered to the baggage 25. If the baggage 25 is blown by an air jet in the sampling room 27 of the adhering matter inspection equipment 1 according to the first embodiment of the present invention, these solid materials, which are not vaporized, are also collected on the collection filter 52 by being peeled off from the baggage 25. Due to the continuous inspection, these solid matters accumulate on the collection filter 52, and cause a degradation of a detection sensitivity of the adhering matter inspection unit 2 by clogging of the collection filter 52 and gases generated from these solid matters.

In the adhering matter inspection equipment 1 according to the present invention, the continuous inspection can be implemented without changing the collection filter 52 at every inspection and without causing problems described above, using the collection filter transportation driving unit 17 to which a rotation function for rotating the hand unit 53 180 degrees around (front-back turn over) is added between the hand unit 53 which holds the collection filter 52 and the transportation arm 54 which supports the hand unit 53.

Figure 14:
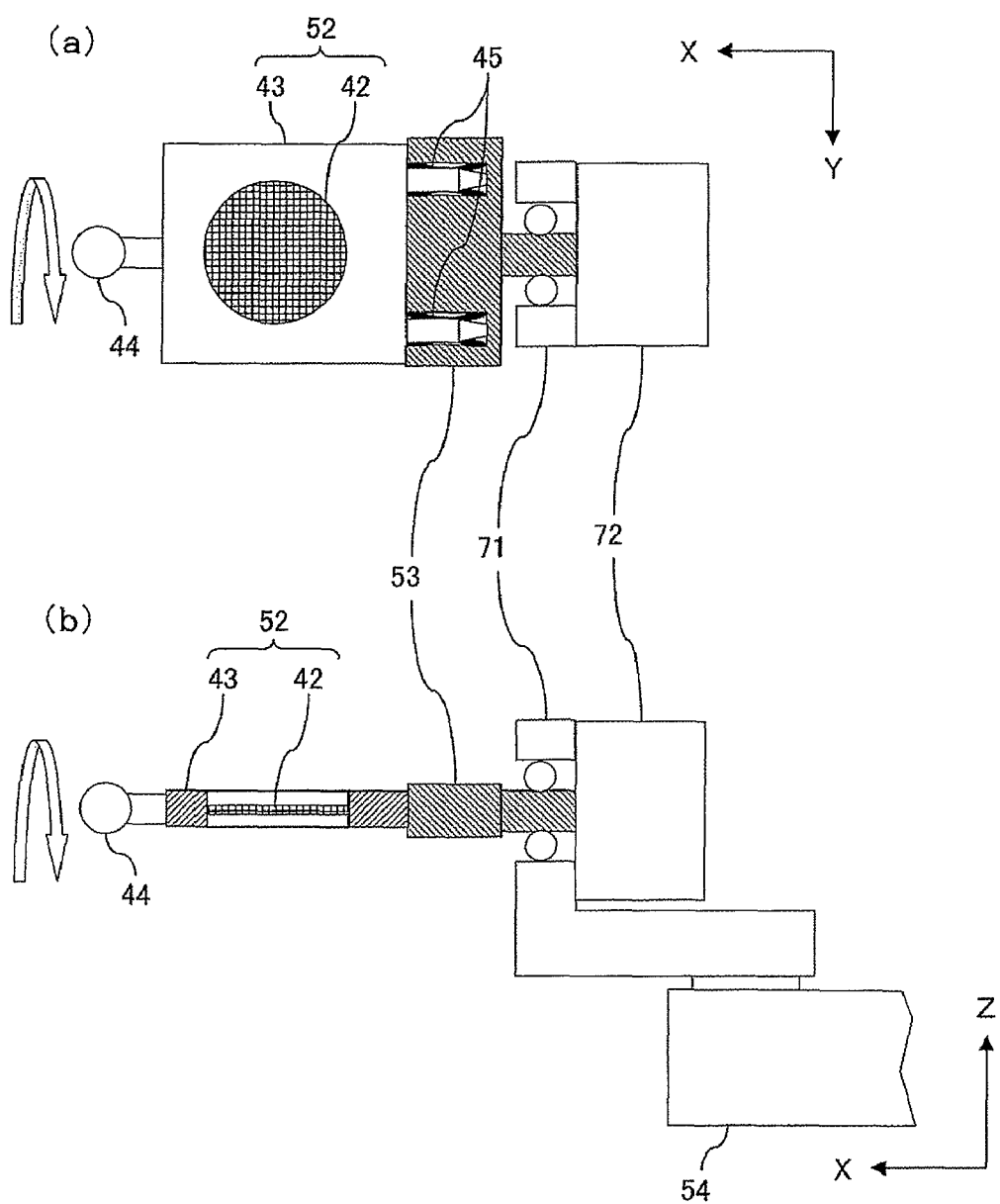
FIG. 14 (a) is a top view including a partial cross section of a collection filter transportation means for explaining the collection filter transportation means to which a rotation function to turn over a front-back of a hand unit is added in the adhering matter inspection equipment according to the first embodiment of the present invention.

FIG. 14 is an illustration including a partial cross section for explaining the collection filter transportation unit 4 capable of continuous inspection in the adhering matter inspection equipment 1 according to the present invention. In FIG. 14, each of the units except for the collection filter 52, the hand unit 53, a part of the transportation arm 54 supporting the hand unit 53 is omitted. FIG. 14 (a) is a cross section passing through centers of the boss 45, and shows a top view as seen from a positive direction of the Z-axis. FIG. 14 (b) is a partial cross sectional view passing through a center of the collection filter 52, and shows a side view as seen from a positive direction of the Y-axis.

The hand unit 53 is supported by the transportation arm 54 via a rotatable bearing 71 and connected to a driving source 72 which rotates the hand unit 53. The driving source 72 is controlled by the transportation unit controller 9 (see FIG. 1).

As described above, a non-penetrating stainless steel filter is used for the collection filter 52. Solid materials adhered to the baggage 25 are collected on a surface of the collection filter 52 by blowing an air jet on the baggage 25 in the sampling room 27. According to the procedure explained in the first embodiment, the collection filter 52 is taken out from the pipe 41 and inserted into the heating unit 18 for inspecting whether or not a dangerous material is included in a sample material. When the collection filter 52 is taken out from the heating unit 18 after completing the inspection, the hand unit 53 holding the collection filter 52 is rotated 180 degrees around to turn over the front-back by driving the driving source 72, and the collection filter 52 is inserted as it is into the pipe 41 of the sampling room 27.

A relatively large solid material which remains on the surface of the collection filter 52 may drop due to the gravity and a vibration during a transportation process by turning over the front-back of the hand unit 53 during the transportation process. Remaining fine particles which remain on the surface of the collection filter 52 without dropping are also peeled off from the collection filter 52 since a gas inside the sampling room 27 is suctioned by the suction unit 16 when the collection filter 52 is inserted into the pipe 41 of the sampling room 27.

According to the adhering matter inspection equipment 1 which is equipped with the collection filter transportation unit 4 described above, since the collection filter 52 can be prevented from clogging by turning over the collection filter 52 at every inspection, an adhering matter inspection equipment 1 can be provided, in which a detection sensitivity of the adhering matter inspection unit 2 is not degraded even if the collection filter 52 is continuously used without changing.

Off course, an inspection of changing the collection filter 52 at every inspection of the baggage 25 is also possible. In this case, a following constitution of the adhering matter inspection equipment 1 is adopted, in which a cassette (not shown) storing a plurality of collection filters 52, a cassette (not shown) storing a used collection filter 52, and a collection filter exchange station on which these cassettes are set, are set in an area where the cassettes can be transported by a collection filter transportation driving unit 17. In the adhering matter inspection equipment 1, the collection filter 52 taken out from the heating unit 18 is inserted in the cassette for storing a used collection filter 52 using the collection filter transportation unit 17. Subsequently, an unused collection filter 52 is taken out from the cassette storing a plurality of the unused collection filters 52 and inserted into the pipe 41 for the next inspection.

Using the adhering matter inspection equipment 1 equipped with the collection filter exchange station (not shown) described above, an adhering matter inspection equipment 1, in which an inspection of the baggage 25 can be implemented always with an unused clean collection filter 52, can be provided.

In addition, by using the adhering matter inspection equipment 1 equipped with the collection filter transportation unit 4, in which the hand unit 53 can rotate 180 degrees around as explained in FIG. 14, and the collection filter exchange station, an inspection method, in which the collection filter 52 is changed, for example, at every 100 inspections, may be possible. That is, by using a procedure identical to the self-cleaning procedure described above, a cleanness level of the collection filter 52 which has been used for the inspection predetermined times is checked by the adhering matter inspection unit 2. If the data processing unit 23 determines that detection accuracy is low due to a large amount of a gas generated from the collection filter 52, the collection filter 52 is inserted in the cassette storing the used collection filter 52 and an unused collection filter 52 is taken out from the cassette storing the plurality of unused collection filters 52, and inserted into the pipe 41 for the next inspection.

Using the adhering matter inspection equipment 1 described above, it is possible to reduce a number of collection filters 52 to be used in a day. In addition, since a cleanness level of the collection filter 52 is always monitored, a certain and high reliable adhering matter inspection equipment 1 can be provided.

Figure 15:
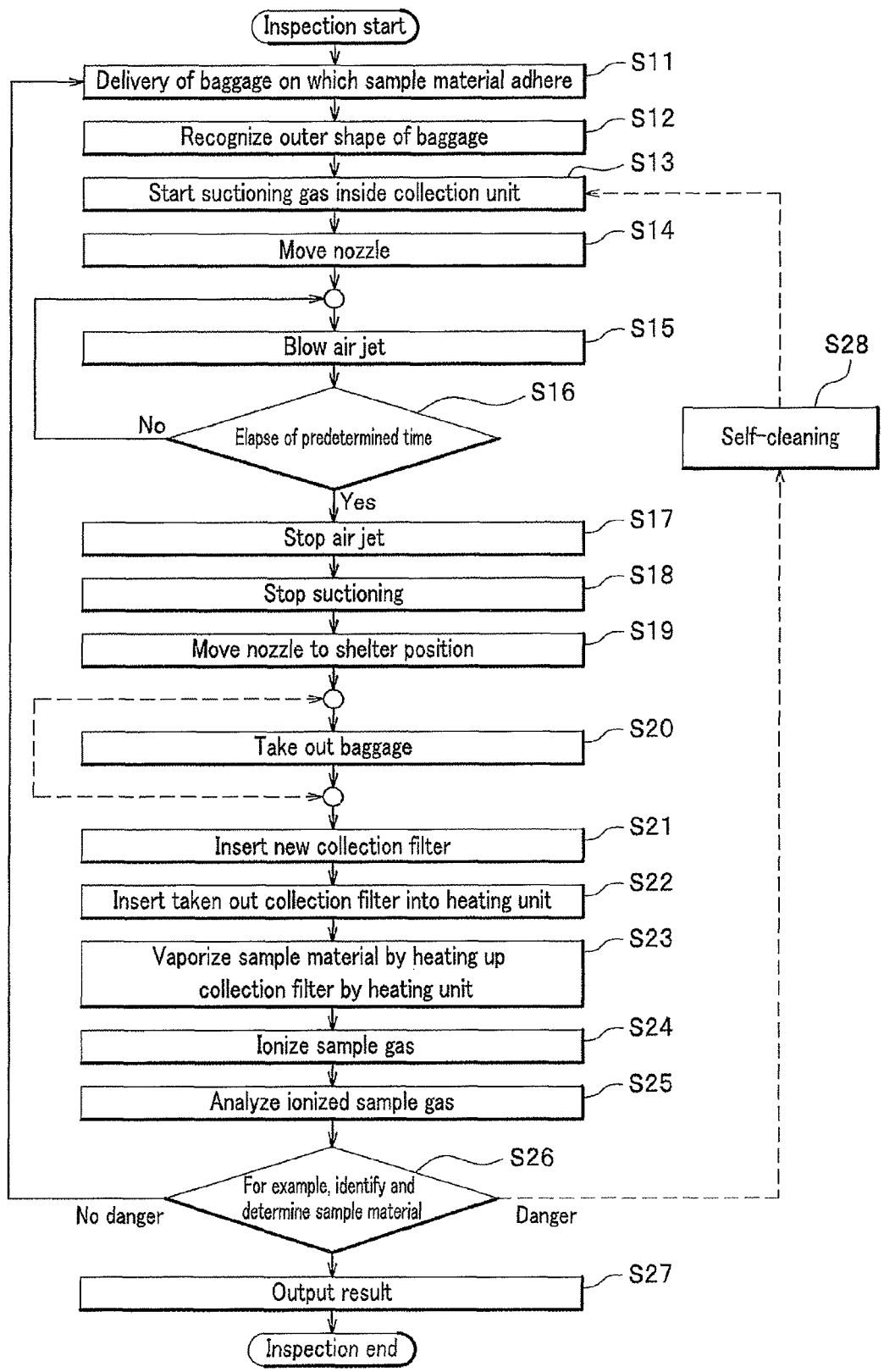
FIG. 15 is a flowchart for explaining a whole process of a normal inspection process of each of the units and a self-cleaning process of the adhering matter inspection equipment according to the present invention.

FIG. 15 is a flowchart showing processes of each operation of the units in the adhering matter inspection equipment 1 according to the present invention described above.

First, a normal inspection process will be explained.

The baggage 25 to which a sample material adheres is delivered to the sampling room 27 by the baggage delivery unit 3 (S11). Then, a size and shape of the baggage 25 are recognized by the baggage recognition unit 12 and the baggage size calculation unit 13 (S12). Next, after a gas inside the sampling room 27 of the adhering matter collection unit 5 is suctioned by driving the suction unit 16 (S13), the nozzle 36 is moved so as to scan a surface of the baggage 25 (S14) and blows an air jet on the surface (S15). After blowing the air jet a predetermined time length, or after scanning a whole surface of the baggage 25 (S16), the blowing of the air jet is stopped (S17). Subsequently, suctioning of a gas inside the sampling room 27 is also stopped by stopping the suction unit 16 (S18). After that, the nozzle 36 is moved to a shelter position (S19), and the baggage 25 is carried out outside the sampling room 27 by the baggage delivery unit 3 (S20). Then, the collection filter 52 is taken out from the pipe 41 of the adhering matter collection unit 5 by the collection filter transportation driving unit 17, while a new collection filter 52 is inserted into the pipe 41 (S21). The collection filter 52 taken out from the pipe 41 is inserted into the heating unit 18 (S22). The collection filter 52 inserted into the heating unit 18 is heated up, thereby a sample material collected on the collection filter 52 is also heated up and vaporizes to generate a sample gas (S23). If the collection filter 52 is heated for a predetermined time, the collection filter 52 is taken out from the heating unit 18 by the collection filter transportation driving unit 17. The sample gas is transported to the ion source unit 19 and transferred to the mass analysis unit 21 after ionization (S24) for mass analysis (S25). The data processing unit 23 determines whether or not there is a dangerous material and identifies the dangerous material based on a result of the mass analysis. If a dangerous material is not detected (S26: no danger), the result is output to the operation panel 11 (S27), and the next inspection starts (jump to S11). If the dangerous material is detected (S26: danger), the result is output to the operation panel 11 to inform the inspector that the dangerous material has been detected (S27), and to waits for an instruction whether or not the self-cleaning process is conducted.

Next, the self-cleaning process will be explained.

If the self-cleaning is instructed by an inspector (S28), an operation flow from S13 to S25 is repeated (however, since the baggage 25 does not exist in the sampling room 27 by being carried out already, the process of S20 is skipped). In the self-cleaning process, an air jet blowing (S15) process is different from that of the normal inspection process described above since the air jet is blown by directing the nozzle 36 toward the inner wall of the sampling room 27, or the arm 39. The self-cleaning (S28) process is repeated until the determination of "no danger" is output in the step S26. If the determination of "no danger" is output in the step S26, the step proceeds to a process for inspecting the next baggage 25 (S11).

(Second Embodiment)

Figure 16:
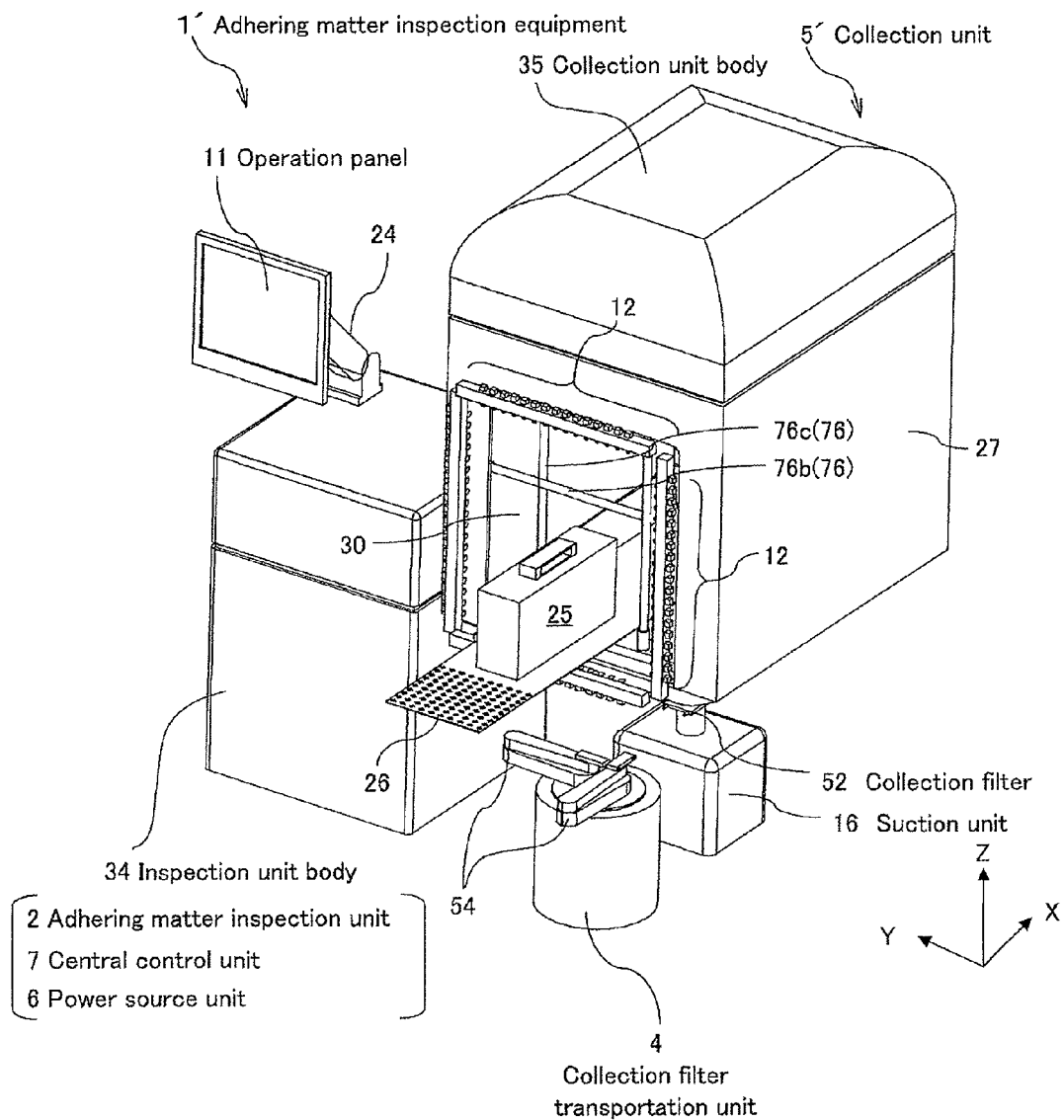
FIG. 16 is a perspective view showing an adhering matter inspection equipment according to a second embodiment of the present invention.
Figure 17:
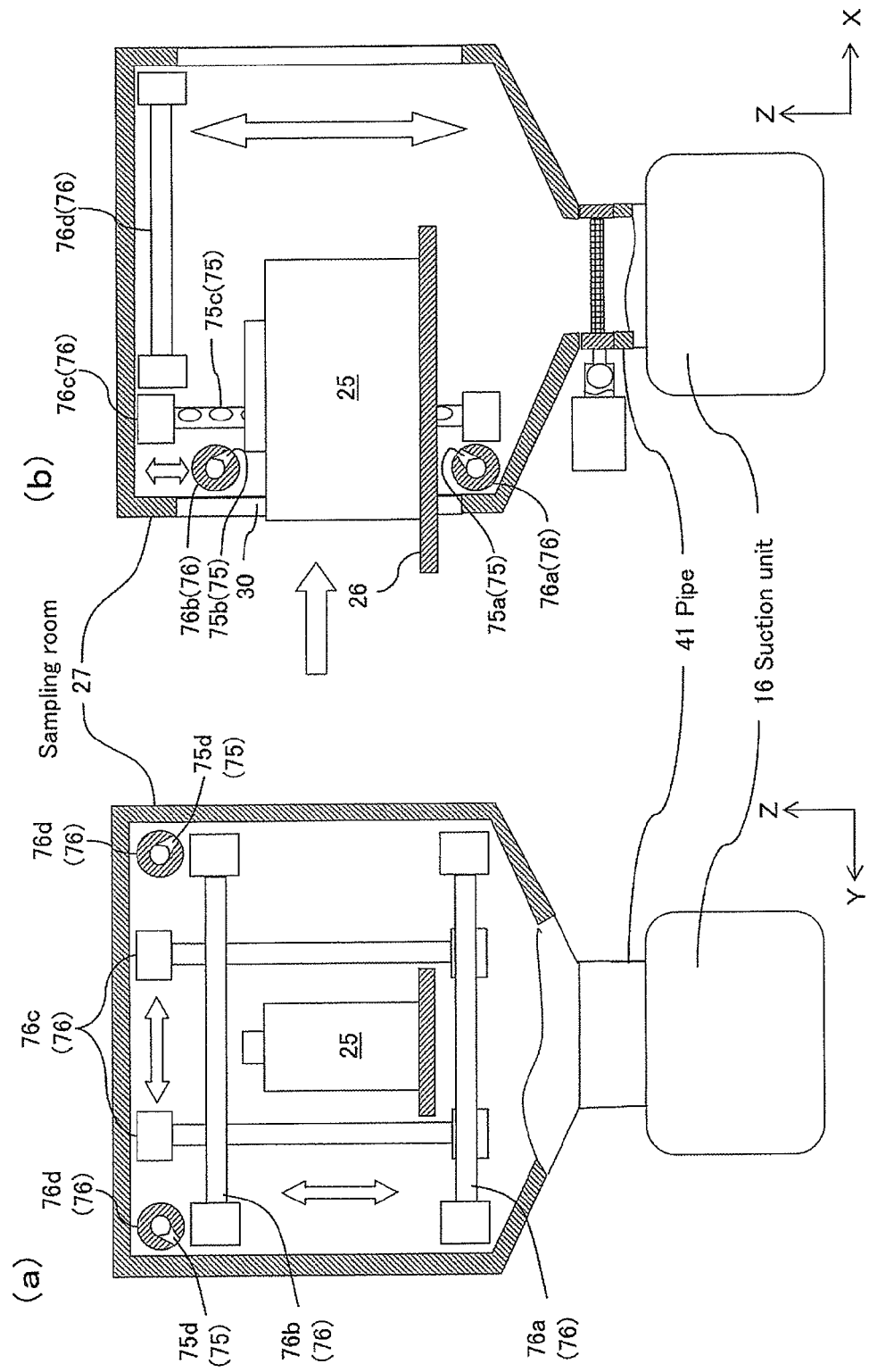
FIG. 17 (*a*) is a front view including a partial cross section for explaining a collection unit of an adhering matter inspection equipment according to the second embodiment of the present invention.

FIG. 16 is a perspective view showing an outer shape of an adhering matter inspection equipment 1' according to a second embodiment of the present invention. FIG. 17 includes a side view and a top view for explaining an adhering matter inspection equipment according to the second embodiment of the present invention. FIG. 17 (a) is a front view including a partial cross sectional view inside the sampling room 27 in an adhering matter collection unit 5' of the adhering matter inspection equipment 1' according to the second embodiment of the present invention.

In FIG. 17 (*a*), a cross section passes through an end face of the gate 30 of the sampling room 27 for a baggage, and the front view is a view as seen from a negative direction of the X-axis. Descriptions of each of units except for nozzle 75 (75*a*, 75*b*, 75*c*, 75*d*) and tube 76 (76*a*, 76*b*, 76*c*, 76*d*) are omitted. FIG. 17 (*b*) is a side view including a partial cross sectional view inside the sampling room 27 in the adhering matter collection unit 5' of the adhering matter inspection equipment 1' according to the second embodiment of the present invention. In FIG. 17 (*b*), a cross section passes through a center of the sampling room 27 and is parallel to a baggage transportation direction of the sampling room 27. The side view is a view as seen from a negative direction of the Y-axis, and descriptions of each of the units except for the nozzle 75 are omitted. Since each constitution of the units of the adhering matter inspection equipment 1' according to the second embodiment except for the nozzle 75 disposed in the adhering matter collection unit 5' is identical to that of the adhering matter inspection equipment 1 according to the first embodiment, the explanation will be omitted.

The baggage recognition unit 12 for detecting a size of the baggage 25 is disposed in a gate shape on a baggage transportation track in front of the gate 30 of the sampling room 27. Since a constitution and effects of the baggage recognition unit 12 are identical to those of the first embodiment, the explanations will be omitted. The baggage 25 arrives at the gate 30 of the sampling room 27 after a size of the baggage 25 is detected by the baggage recognition unit 12 and a supposed outer shape is calculated by the adhering matter collection unit 5.

As shown in FIGS. 7 (*a*), (*b*), the nozzle 75 of the adhering matter inspection equipment 1' according to the second embodiment includes four nozzle systems, that is, a nozzle 75*a* for blowing an air jet on a bottom surface of the baggage 25, a nozzle 75*b* for blowing the air jet on an upper surface of the baggage 25, nozzles 75*c*, 75*c* for blowing the air jet on side surfaces of the baggage 25, and a nozzle 75*d* for blowing the air jet on an inner wall of the sampling room 27. The nozzle 75*a* is disposed on a cylindrical tube 76*a*. The cylindrical tube 76*a* is set at a position 3 cm below from a transportation track of the tray 26 at the gate 30, and has a length longer than 40 cm which is a width of the baggage 25 capable of being inspected. The cylindrical tube 76*a* is rotatable around a central axis of the tube 76*a*. Twenty pieces of the nozzles 75*a* having a diameter of 2 mm are disposed on the tube 76*a* inclined at 30 degrees to a bottom surface of the tray 26 toward a transportation direction at intervals of 3 cm.

The nozzle 75*b* is disposed on a pair of cylindrical tubes 76*b*. The cylindrical tubes 76*b* are set at a position of the gate 30 higher than the baggage 25, can travel linearly downward, have a length longer than 40 cm which is the width of the baggage 25 capable of being inspected, and are rotatable around a central axis of the tubes 76*b*. Twenty pieces of the nozzles 75*b* having a diameter of 2 mm are disposed on the tube 76*b* inclined at 30 degrees to an upper surface of the tray 26 toward a transportation direction at intervals of 3 cm.

The nozzles 75*c* are disposed on the cylindrical tubes 76*c*. Each of the cylindrical tubes 76*c* is set on both sides inside the sampling room 27, can travel linearly in a lateral direction, has a length longer than 50 cm which is a height of the baggage 25, and is rotatable around a central axis of the tube 76*c*. Twenty five pieces of the nozzles 75*c* having a diameter of 2 mm are disposed on the tube 76*c* inclined at 30 degrees to a surface parallel to a transportation track of the tray 26 toward a transportation direction at intervals of 3 cm.

The nozzle 75*d* is disposed on a cylindrical tube 76*d*. The cylindrical tube 76*d* can travel linearly downward from a position higher than the baggage 25, and it is disposed at a position 3 cm away from the inner wall of the sampling room 27. Thirty pieces of the nozzle 75*d* having a diameter of 2 mm are disposed on the tube 76*d* inclined at 30 degrees to the inner wall of the sampling room 27 toward a downward direction at intervals of 3 cm.

An air jet blowing procedure of the adhering matter inspection equipment 1' according to the second embodiment will be explained.

An arrival time of the baggage 25 at the gate 30 is calculated by the collection unit controller 10 based on a signal detection time of the baggage recognition unit 12, a transportation speed of the baggage, and a distance between installation positions of the baggage recognition unit 12 and the gate 30. Off course, it is possible to install a sensor for detecting the arrival of the baggage 25 at the gate 30.

Before the arrival of the baggage 25 at the gate 30 of the sampling room 27, the nozzle 75*b* is moved to a position 5 cm away from a supposed height of the baggage 25 calculated by the baggage size calculation unit 13.

At the same time, the nozzle 75*c* is moved to a position 5 cm apart from a supposed width of the baggage 25 calculated by the baggage size calculation unit 13.

At the time, the suction unit 16 for suctioning a gas inside the sampling room 27 and the compression gas generating unit 15 (see FIG. 1) are also driven. When the collection unit controller 10 determines that the baggage 25 arrives at the gate 30, an air valve (not shown) connecting the nozzle 75 (75*a*, 75*b*, 75*c*) and the compression gas generating unit 15 is opened, and a compressed gas is supplied to the nozzle 75 (75*a*, 75*b*, 75*c*). According to a supposed maximum width and supposed maximum height of the baggage 25, which are calculated by the baggage size calculation unit 13, at a place where each of the nozzles 75 is arranged, the nozzles 75*b*, 75*c* are controlled and moved in movable directions, respectively by the nozzle driving unit 14. When the collection unit controller 10 determines that the baggage 25 has passed the position of the nozzle 75, the air valve (not shown). is closed, and the blowing of the air jet is stopped. After that, the cylindrical tube 76*a* on which the nozzle 75*a* is disposed is rotated so that the nozzle 75*a* is inclined at 30 degrees to the inner wall of the sampling room 27. After the cylindrical tube 76*a* is rotated, the air valve (not shown) connecting the nozzles 75*a*, 75*d* and the compression gas generating unit 15 is opened, and the air jet is blown toward the inner wall of the sampling room 27 by supplying the compressed gas to the nozzles 75*a*, 75*d*. The nozzle 75*d* is lowered to a bottom surface of the sampling room 27, while blowing the air jet on the inner wall of the sampling room 27.

When the collection unit controller 10 determines that the nozzle 75*d* has arrived at the bottom surface of the sampling room 27, the air valve (not shown) is closed and the nozzle 75*d* is raised to a shelter position. During the air jet blowing, the baggage 25 is being carried by the carrying tray 26.

Subsequently, the collection filter 52 is taken out from the pipe 41, and as shown in FIG. 7, the collection filter 52 is inserted into the heating unit 18 by the collection filter transportation driving unit 17, and heated and vaporized in the heating unit 18. Since means for mass analysis and means for identifying a dangerous material from a result of the mass analysis are identical to those of the first embodiment, the explanations will be omitted.

Figure 18:
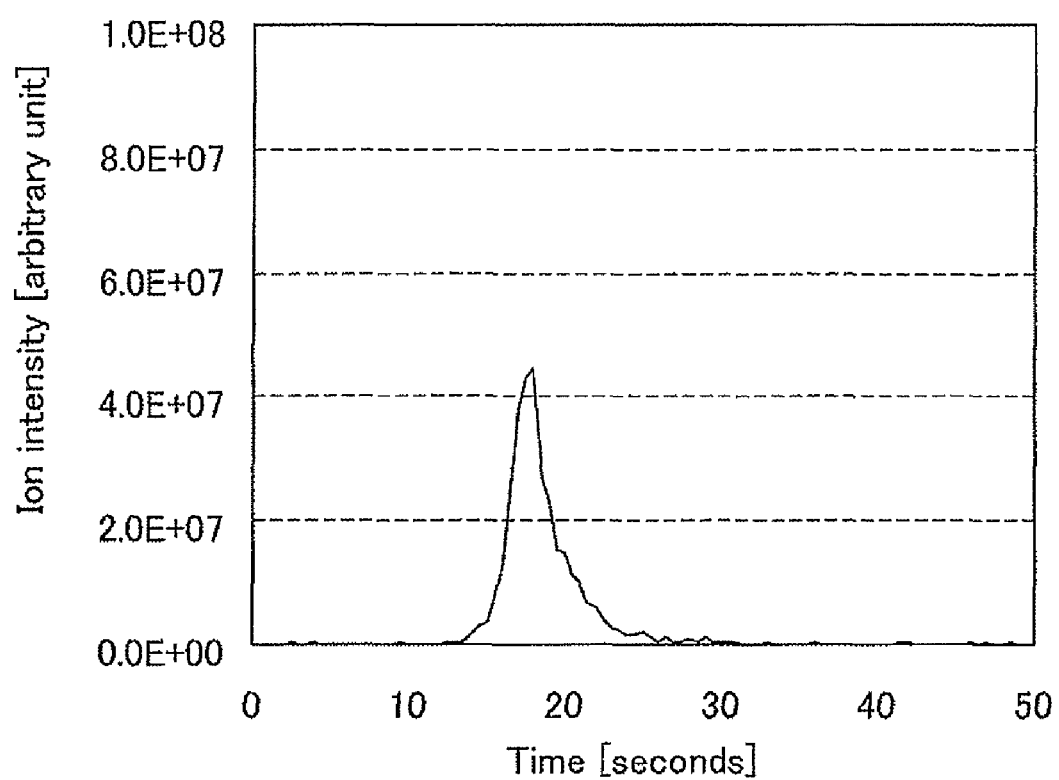
FIG. 18 is a figure showing a time dependence of a signal intensity of a mass-to-charge ratio of a C4 explosive component detected from a baggage to which C4 explosive particles adhere in the adhering matter inspection equipment according to the second embodiment of the present invention.

FIG. 18 is a figure showing a result of an inspection of the baggage 25 to which C4 explosive particles adhere, by using a constitution of an adhering matter inspection equipment according to the second embodiment. In FIG. 18, a vertical axis indicates ion intensity with an arbitrary unit, and a horizontal axis indicates a time by seconds. As shown in FIG. 18, a clear signal of the C4 explosive component has been obtained. From the result, it has been proved that a component of the C4 explosive can be detected by the data processing unit 23, by peeling off the C4 explosive particles by the air jet from the baggage 25 to which the C4 explosive particles adhere, by collecting the C4 explosive particles on the collection filter 52, and by vaporizing the C4 explosive particles, using the adhering matter inspection equipment according to the second embodiment. In the adhering matter inspection equipment composed of a constitution according to the embodiment, it has been proved from the experiments that an average collection rate of the C4 explosive from the baggage 25 is 4%.

According to the adhering matter inspection equipment 1' of the second embodiment, an adhering matter inspection equipment 1' can be provided, in which since an inspection for determining whether or not explosive fine particles exist on the baggage 25 can be implemented without stopping the baggage 25 in the sampling room 27, a high throughput of the inspection can be achieved, and there is no possibility to cause a breakage and contamination of the baggage 25. In addition, a skilled inspector is not required, and the inspection is conducted under a constant condition without touching the baggage 25.

In the adhering matter inspection equipment 1 according to the first embodiment and the adhering matter inspection equipment 1' according to the second embodiment described above, it is one of the advantages that an inspection apparatus for observing inside the baggage such as a well-known X-ray transmission spectrometer can be installed in the sampling room 27. Therefore, since an adhering matter inspection equipment which is capable of a baggage inspection combining the adhering matter inspection equipment according to the present invention and an inside inspection apparatus such as a commonly used X-ray transmission spectrometer can be achieved, a more certain and higher reliable adhering matter inspection equipment for a baggage can be provided.

In addition, in the adhering matter inspection equipment 1 according to the first embodiment and the adhering matter inspection equipment 1' according to the second embodiment, a photodetector composed of the phototransmitter 32 and the photoreceiver 33 is used for the baggage recognition unit 12. However, other than the photodetector, means for detecting a baggage size from baggage images which are photographed by a plurality of cameras from lateral directions and top and bottom directions of the baggage 25 and means for detecting the baggage size from a baggage image obtained by the X-ray transmission spectrometer described above may be used.

(Third Embodiment)

In addition, in the adhering matter inspection equipment 1 according to the first embodiment and the adhering matter inspection equipment 1' according to the second embodiment described above, the explanations have been made assuming that the baggage 25 is the inspection object. However, a human body may be the inspection object too.

Figure 19:
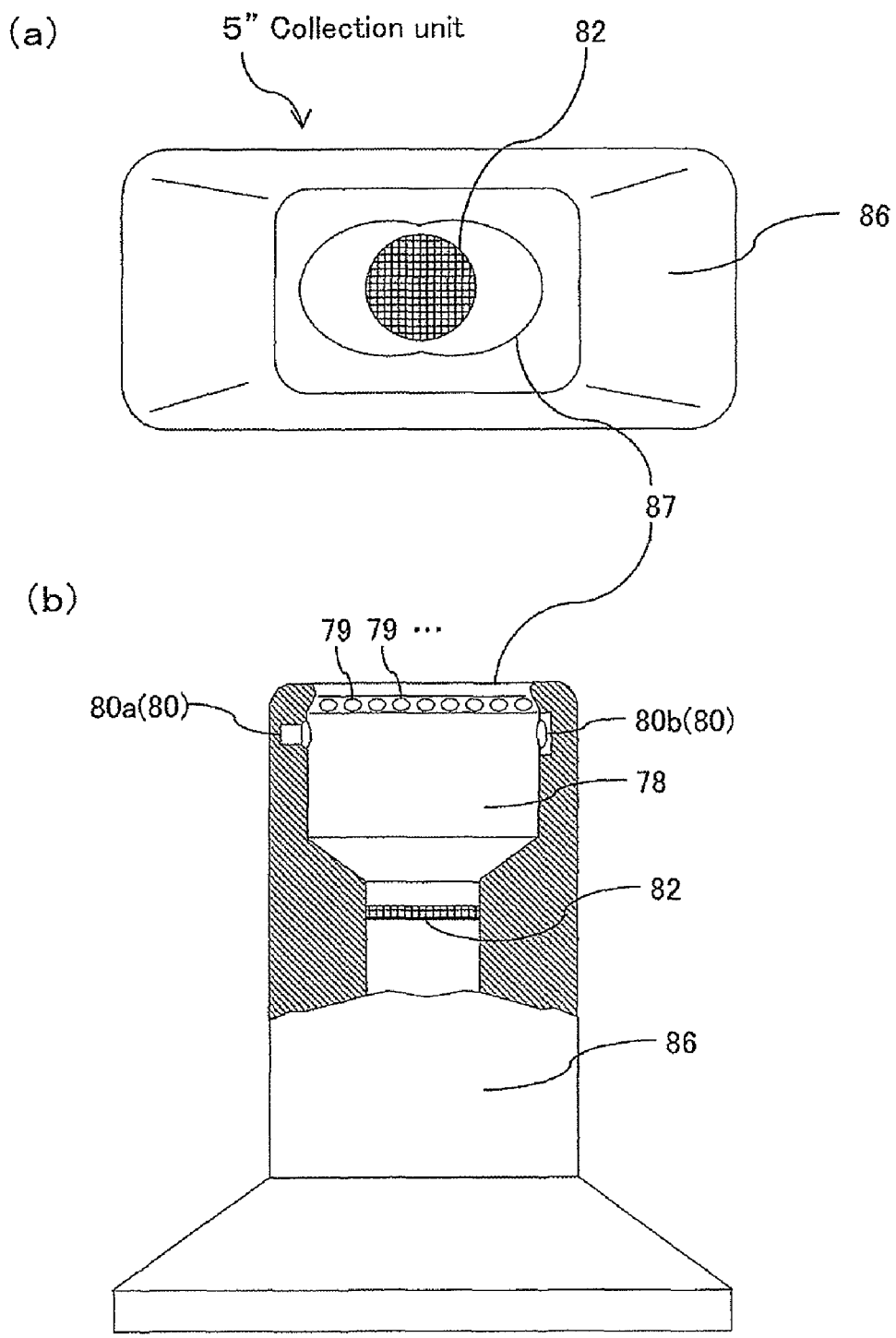
FIG. 19 (*a*) is a top view including a partial cross section for explaining a collection unit of the adhering matter inspection equipment according to a third embodiment of the present invention.

FIG. 19 is an illustration showing a side view and a top view for explaining a collection unit 5" according to a third embodiment of an adhering matter inspection equipment 1", in which a human body is assumed as the inspection object. FIG. 19 (a) is a top view of a sampling room 78 in the collection unit 5" of the adhering matter inspection equipment 1" according to the third embodiment of the present invention. FIG. 19 (b) is a side view including a partial cross section inside a sampling room 78 in the collection unit 5" of the adhering matter inspection equipment 1" according to the third embodiment of the present invention. In FIG. 19 (b), the cross section passes through a center of the sampling room 78.

The adhering matter inspection equipment 1" according to the third embodiment is an equipment for inspecting a lower arm of a human body (inspection object). The collection unit 5" according to the third embodiment is composed of the sampling room 78 in which an arm is actually inserted, a nozzle 79 for blowing an air jet on the arm, detector 80 (80a, 80b) for detecting an insertion of the arm, the compression gas generating unit 15 (see FIG. 1) for supplying a compressed gas to the nozzles 79, 79, a collection filter 82 for collecting a sample material which is peeled off from the arm, the suction unit 16 (see FIG. 1) for suctioning a gas inside the sampling room 78 through the collection filter 82, the power source unit 6 (see FIG. 1) for driving the units described above, and a controller (not shown) for controlling the units described above. In FIG. 19, each of the units except for the nozzle 79 and the detector 80 for detecting the insertion of the arm is stored in a body 86.

Hereinafter, an inspection procedure of a human body using the collection unit 5" of the adhering matter inspection equipment 1" according to the third embodiment will be explained.

An arm insertion slot 87 according to the embodiment is disposed above the sampling room 78. An examinee inserts both arms more deeply than the wrist in the arm insertion slot 87. A detection of the insertion of the arms by the detector 80 for detecting the arm, which is set at the insertion slot 87 of the sampling room 78, is transmitted to the control unit. The detector 80 is composed of the phototransmitter 80a for transmitting a light and the photoreceiver 80b for receiving the light from the phototransmitter 80a. The photoreciever 80b transmits a signal when the light from the phototransmitter 80a is not received. The control unit drives the suction unit 16 (see FIG. 1) after receiving a detection signal, and subsequently drives the compression gas generating unit 15 (see FIG. 1) a few seconds later after the suction unit 16 is driven. Considering a time needed for inserting the arm, the few seconds are set before driving the compression gas generating unit 15. In addition, in the embodiment, a turbofan is used for the compression gas generating unit 15. The nozzles 79, 79, . . . according to the embodiment are disposed at the insertion slot 87 of the sampling room 78 on both sides of the insertion slot 87 by being inclined downward at intervals of 2 cm so that the air jet can be blown from both directions of a palm and back of one's hand. Twenty five nozzles 79, 79, . . . having a diameter of 2 mm are disposed on each side. A distance between the nozzles 79, 79, . . . and the arm of the examinee is fixed. As described in the first embodiment, a size of the arm insertion slot 87 of the sampling room 78 is designed so that the distance between the nozzles 79, 79, . . . and the arm of the examinee may be from 3 cm to 9 cm so as to blow the air jet having a blowing speed of 40 m/s to 130 m/s on a surface of the arm at an angle of about 30 degrees.

When the compression gas generating unit 15 is driven, an air jet is blown on the arm from the nozzles 79, 79, . . . .

If the examinee feels the air jet, the examinee slowly draws out the arm from the sampling room 78. A detection of drawing out of the arm by the detector 80 for detecting the arm, which is set at the arm insertion slot 87 of the sampling room 78, is transmitted to the control unit. The control unit stops the compression gas generating unit 15 when the detection signal is received, and subsequently stops the suction unit 16. According to the procedure described above, a sample material adhered to the lower arm of the examinee can be peeled off. In a lower portion of the sampling room 78, a collection filter 82 is inserted and a sample material is collected on the collection filter 82.

Since constitutions of the collection filter 82, the collection filter transportation driving unit 17, and the adhering matter inspection unit 2 are identical to those of the first embodiment, and the procedures for taking out the collection filter 82 from the sampling room 78, for inserting the collection filter 82 into the heating unit 18, for vaporizing the sample material, for ionizing, for mass-analyzing, and for checking whether or not a dangerous material exists and identifying the material are identical to those of the first embodiment, the explanations will be omitted.

Figure 20:
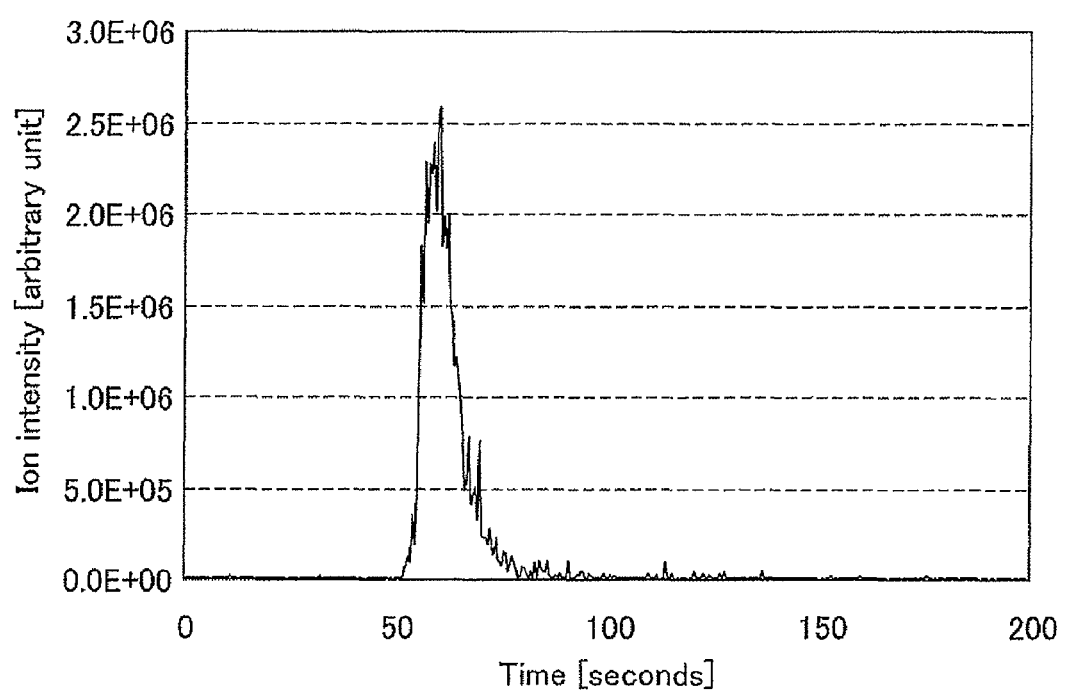
FIG. 20 is a figure showing a time dependence of a signal intensity of a mass-to-charge ratio of a C4 explosive component detected from a hand with which C4 explosive particles are touched in the adhering matter inspection equipment according to the third embodiment of the present invention.

FIG. 20 is a figure showing a result of an inspection of a hand with which the C4 explosive is actually touched, by using the adhering matter inspection equipment 1" according to the third embodiment. In FIG. 20, the vertical axis indicates signal intensity with an arbitrary unit, and the horizontal axis indicates a time by seconds. As shown in FIG. 20, a clear signal has been obtained at a detection point of the C4 explosive. From the result, it has been proved that the C4 explosive can be detected by using the adhering matter inspection equipment according to the third embodiment, in which C4 explosive particles are peeled off by the air jet from the hand with which the C4 explosive is touched, collected on the collection filter 82, vaporized by the heating unit 18, and detected by the mass analysis unit 21.

In the adhering matter inspection equipment 1" according to the third embodiment, the inspection object is the lower arm portion of a human being. However, the inspection object can be widened by changing a shape of the insertion slot 87 of the sampling room 78. For example, shoes of the examinee, mails (by making a size of the insertion slot as large as that of mails of a mail post), and tickets such as a boarding ticket can be inspected as the inspection object. In addition, in the adhering matter inspection equipment 1" according to the third embodiment, it is possible to inspect a whole human body as the inspection object by disposing the sampling room 78 in which head-to-toe of a human being can be scanned by the nozzles 79, 79, . . . .

Meanwhile, in the adhering matter inspection equipments 1, 1', and 1" according to the first, second, and third embodiments, the collection filters 52, 82 are transported by the collection filter transportation driving unit 17. However, by manually transporting the collection filters by the inspector without using the collection filter transportation driving unit 17, it is also possible to peel off a sample material from the baggage 25, to collect the sample material, and to inspect the material, which are the purposes of the present invention. Similarly, with respect to the air jet blowing, the air jet is automatically blown using the nozzle driving unit 14 in the adhering matter inspection equipments 1, 1', and 1" according to the first, second, and third embodiments described above. However, the sample material can be peeled off from the baggage 25, can be collected, and can be inspected by manually scanning the nozzle by the inspector on a surface of the inspection object so that the air jet having a blowing speed of 40 m/s to 130 m/s can be blown on the surface of the inspection object. In this case, the baggage recognition unit 12 is not required, thereby a less expensive and simple adhering matter inspection equipment for a baggage can be provided.

In addition, in the adhering matter inspection equipments 1, 1', and 1" according to the first, the second, and the third embodiments, the collection filters 52, 82 are used as a collecting means for a sample material. However, the collecting means is not limited to the collection filters 52, 82. For example, an impactor, which is a well-know technology, may be set between the sampling room 27 and the suction unit 16. A board on which a sample material of the impactor is deposited is transported by the collection filter transportation driving unit 17 of the first, or the second, or the third embodiment, or transported manually by the inspector to the heating unit 18. As a result, a purpose of the present invention can be achieved, in which adhered fine particles can be peeled off from the baggage 25, can be collected, and can be inspected.

In addition, in the adhering matter inspection equipments 1, 1', and 1" according to the first, the second, and the third embodiments, a mass analysis means is used for the adhering matter inspection unit 12. However, the adhering matter inspection unit is not limited to the mass analysis means. Any apparatus may be used as long as the apparatus can identify a sample material adhered to the inspection object. For example, an adhering matter inspection equipment using a well-known chemiluminescence method may be applied to the present invention, in which a sample material vapor vaporized by the hating unit 18 is separated by gas chromatography, and an emission of the separated vapor is detected by reacting the vapor with a chemiluminescence reagent to identify unknown materials. In addition, an adhering matter inspection equipment using a well-known ion mobility measurement method can be applied to the present invention, in which the vapor is ionized by radio isotopes inside the ion source unit 19, and a ion mobility is detected by introducing the ions of the vapor in a drift tube to identify the unknown materials.

The invention claimed is:

1. An adhering matter inspection equipment, comprising:
    a blowing unit for peeling off a sample material from an outer surface of an inspection object by blowing a gas flow on the inspection object;
    a collection unit for collecting a sample material;
    an inspection unit for analyzing the sample material collected by the collection unit; and
    at least one nozzle for blowing the gas flow on a surface of the inspection object with a blowing speed of not less than 20 m/s,
    wherein the collection unit comprises:
    a recognition unit for recognizing an outer shape of the inspection object;
    a calculation unit for calculating a baggage size by using a signal from the recognition unit; and
    a nozzle driving unit for moving the nozzle based on the outer shape calculated by the calculation unit.

2. The adhering matter inspection equipment according to claim 1, further comprising:
    a suction unit for introducing a gas including the peeled off sample material to a collection filter.

3. The adhering matter inspection equipment according to claim 1, further comprising:
    a delivery unit for delivering the inspection object to the collection unit.

4. The adhering matter inspection equipment according to claim 1, further comprising:
    a transportation unit for transporting a collection filter to the inspection unit.

5. The adhering matter inspection equipment according to claim 4,
    wherein the transportation unit has a function to turn over the collection filter.

6. The adhering matter inspection equipment according to claim 1,
wherein the recognition unit comprises at least a pair of a phototransmitter for emitting a light and a photoreceiver for receiving the light.

7. The adhering matter inspection equipment according to claim 1,
wherein the inspection unit comprises:
a heating unit for heating up the collection filter to generate a sample gas by vaporizing the collected sample material; and
an analysis unit for analyzing the sample gas to identify the sample material.

8. The adhering matter inspection equipment according to claim 7,
wherein the analysis unit comprises:
an ion source unit for introducing the sample gas and ionizing the sample gas;
a mass analysis unit for introducing the ionized sample gas, for separating components of the ionized sample gas based on a difference in mass of each of the components, and for obtaining mass spectral data of the sample gas; and
a data processing unit for identifying the sample gas from the mass spectral data.

9. The adhering matter inspection equipment according to claim 1,
wherein the nozzle driving unit moves the nozzle to a predetermined position, and the nozzle blows the gas flow on an inner wall of the collection unit and/or an arm holding the nozzle.

10. The adhering matter inspection equipment according to claim 1, further comprising:
an inside inspection apparatus for observing inside the inspection object.

11. A method for inspecting an adhering matter, comprising steps of:
a step for recognizing an outer shape of an inspection object to which a sample material adheres;
a step for calculating baggage size based on recognition of the outer shape;
a step for moving a nozzle based on the outer shape;
a step for blowing a gas flow on an outer surface of the inspection object with a blowing speed of not less than 20 m/s, while moving a blowing position of the gas flow;
a step for collecting the sample material which is peeled off from the inspection object;
a step for generating a sample gas by heating up a collection filter to vaporize the collected sample material; and
a step for identifying the sample material by analyzing the generated sample gas.

12. The method for inspecting an adhering matter according to claim 11, further comprising a step of:
a step for moving the nozzle to a predetermined position; and
a step for blowing the gas flow on an inner wall of a collection unit that collects the sample material and/or an arm holding the nozzle.

* * * * *